(12) United States Patent
Laude et al.

(10) Patent No.: US 12,313,531 B2
(45) Date of Patent: *May 27, 2025

(54) METHODS OF CHARACTERIZING A URINE SAMPLE

(71) Applicant: Genotox ID LLC, Austin, TX (US)

(72) Inventors: Nicholas D. Laude, Pflugerville, TX (US); William S. Edgemond, Round Rock, TX (US); Keqin Gregg, Austin, TX (US)

(73) Assignee: Genotox ID LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/623,412

(22) Filed: Apr. 1, 2024

(65) Prior Publication Data

US 2024/0426745 A1   Dec. 26, 2024

Related U.S. Application Data

(63) Continuation of application No. 17/391,876, filed on Aug. 2, 2021, now Pat. No. 11,946,861, which is a continuation of application No. 16/564,170, filed on Sep. 9, 2019, now Pat. No. 11,079,320, which is a continuation of application No. 15/730,433, filed on Oct. 11, 2017, now Pat. No. 10,451,544.

(60) Provisional application No. 62/406,692, filed on Oct. 11, 2016.

(51) Int. Cl.
G01N 21/31     (2006.01)
G01N 21/64     (2006.01)
G16H 50/20     (2018.01)

(52) U.S. Cl.
CPC ....... *G01N 21/3103* (2013.01); *G01N 21/314* (2013.01); *G01N 21/3151* (2013.01); *G01N 21/6486* (2013.01); *G16H 50/20* (2018.01); *C12Q 2537/165* (2013.01)

(58) Field of Classification Search
CPC ......... C12Q 2537/165; G01N 21/3103; G01N 21/314; G01N 21/3151; G01N 21/6486; G16H 50/20

See application file for complete search history.

(56) References Cited

U.S. PATENT DOCUMENTS

| | | | |
|---|---|---|---|
| 5,547,859 | A | 8/1996 | Goodman et al. |
| 6,012,058 | A | 1/2000 | Fayyad et al. |
| 6,602,662 | B1 | 8/2003 | Köster et al. |
| 6,615,205 | B1 | 9/2003 | Cereghini et al. |
| 7,867,714 | B2 | 1/2011 | Ehrich et al. |
| 9,310,378 | B2 | 4/2016 | Becker |
| 11,079,320 | B2 | 8/2021 | Laude et al. |

(Continued)

FOREIGN PATENT DOCUMENTS

| | | |
|---|---|---|
| WO | WO 2008/155549 A2 | 12/2008 |
| WO | WO 2011/162589 A1 | 12/2011 |

OTHER PUBLICATIONS

Akutsu et al., "Applicability of ELISA detection of statherin for forensic identification of saliva," International journal of legal medicine, Sep. 2010, 124:493-8.

(Continued)

*Primary Examiner* — Jennifer Wecker
(74) *Attorney, Agent, or Firm* — Fish & Richardson P.C.

(57) ABSTRACT

This disclosure relates to methods of characterizing a urine sample from a subject.

26 Claims, 6 Drawing Sheets
(4 of 6 Drawing Sheet(s) Filed in Color)
Specification includes a Sequence Listing.

(56) References Cited

U.S. PATENT DOCUMENTS

| | | | |
|---|---|---|---|
| 2008/0163824 | A1 | 7/2008 | Moser et al. |
| 2012/0100996 | A1 | 4/2012 | Hubert et al. |
| 2012/0130061 | A1 | 5/2012 | Himmelreich et al. |
| 2012/0141450 | A1 | 6/2012 | Perez-Rasilla et al. |
| 2012/0270212 | A1 | 10/2012 | Rabinowitz et al. |
| 2013/0047275 | A1 | 2/2013 | Held et al. |
| 2016/0069743 | A1* | 3/2016 | McQuilkin ............ A22B 5/007 356/416 |
| 2016/0145684 | A1 | 5/2016 | McCarty et al. |
| 2018/0328912 | A1 | 11/2018 | McCarty et al. |
| 2019/0170639 | A1 | 6/2019 | Laude et al. |
| 2020/0116628 | A1 | 4/2020 | Laude et al. |
| 2024/0027334 | A1 | 1/2024 | McCarty et al. |

OTHER PUBLICATIONS

Ballman et al., "Faster cyclic loess: normalizing RNA arrays via linear models," Bioinformatics, Nov. 2004, 20(16):2778-86.

Betsou et al., "Construction and evaluation of internal control DNA for PCR amplification of Chlamydia trachomatis DNA from urine samples, " Journal of clinical microbiology, Mar. 2003, 41(3):1274-6.

Bharadwaj et al., "Multipotential differentiation of human urine-derived stem cells: potential for therapeutic applications in urology," Stem cells, Sep. 2013, 31(9):1840-56.

Borgatti, "How to explain hierarchical clustering," Oct. 1994, Connections, 17(2): 81-84, 4 pages.

Bruse et al., "Improvements to bead-based oligonucleotide ligation SNP genotyping assays," Biotechniques, Nov. 2008, 45(5):559-71.

Bush et al., "The US mandatory guidelines for federal workplace drug testing programs: current status and future considerations," Forensic Science International, Jan. 30, 2008, 174(2-3):111-9.

Callister et al., "Normalization approaches for removing systematic biases associated with mass spectrometry and label-free proteomics," Journal of proteome research, Feb. 3, 2006, 5(2):277-86.

Castella et al., "Forensic identification of urine samples: a comparison between nuclear and mitochondrial DNA markers," International journal of legal medicine, Mar. 2006, 120:67-72.

Charretier et al., "Mass spectrometry methods for predicting antibiotic resistance," Proteomics—Clinical Applications, Oct. 2016, 10(9-10):964-81.

Cho et al., "Biomarker Characterization by MALDI-TOF/MS," Advances in clinical chemistry, Jan. 2015, 69:209-54.

D'Andrade et al., "U-statistic hierarchical clustering," Psychometrika, Mar. 1978, 43:59-67.

Deininger et al., "Normalization in MALDI-TOF imaging datasets of proteins: practical considerations," Analytical and bioanalytical chemistry, Jul. 2011, 401:167-81.

Duncan et al., "Applications of MALDI mass spectrometry in clinical chemistry," Clinical chemistry, Jan. 2016, 62(1):134-43.

Edwards et al., "DNA sequencing using biotinylated dideoxynucleotides and mass spectrometry," Nucleic acids research, Nov. 2001, 29(21):e104, 6 pages.

Ehrich et al., "Quantitative high-throughput analysis of DNA methylation patterns by base-specific cleavage and mass spectrometry," Proceedings of the National Academy of Sciences, Nov. 2005, 102(44):15785-90.

Fakruddin et al., "Nucleic acid amplification: Alternative methods of polymerase chain reaction," Journal of Pharmacy and Bioallied Sciences, Oct. 2013, 5(4):245-52.

Gabriel et al., "SNP genotyping using the Sequenom MassARRAY iPLEX platform," Current protocols in human genetics, Jan. 2009, 60(1):2-12.

Gaudet et al., "Allele-specific PCR in SNP genotyping.", Methods Mal. Biol., 2009, 578:415-424.

Griffin et al., "Label-free, normalized quantification of complex mass spectrometry data for proteomic analysis," Nature biotechnology, Jan. 2010, 28(1):83-9.

Hajduk et al., "Challenges in biomarker discovery with MALDI-TOF MS," Clinica Chimica Acta, Jul. 2016, 458:84-98.

Howell et al., "Dynamic allele-specific hybridization," Nature biotechnology, Jan. 1999, 17(1):87-8.

Johnson, Stephen C., "Hierarchical Clustering Schemes," Sep. 1967, Psychometrika, 32(3):241-254, 14 pages.

Jones et al., "Temporal temperature gradient electrophoresis for detection of single nucleotide polymorphisms," Single Nucleotide Polymorphisms: Methods and Protocols, Jan. 2009, 578:153-65.

Kakoi et al., "Individual identification of racehorses from urine samples using a 26-plex single-nucleotide polymorphism assay," Journal of Forensic Sciences, Jan. 2013, 58(1):21-8.

Kanungo et al., "An efficient k-means clustering algorithm: Analysis and implementation," IEEE transactions on pattern analysis and machine intelligence, Jul. 2002, 24(7):881-92.

Karger et al., "Current developments to use linear MALDI-TOF spectra for the identification and typing of bacteria and the characterization of other cells/organisms related to infectious diseases, " Proteomics—Clinical Applications, Oct. 2016, 10(9-10):982-93.

Koboldt et al., "The next-generation sequencing revolution and its impact on genomics," Cell, Sep. 26, 2013, 155(1):27-38.

Kriegsmann et al., "MALDI TOF imaging mass spectrometry in clinical pathology: a valuable tool for cancer diagnostics," International journal of oncology, Dec. 4, 2014, 46(3):893-906.

Kwok et al., "Methods for genotyping single nucleotide polymorphisms," Annual review of genomics and human genetics, Sep. 2001, 2(1):235-58.

Lou et al., "A SNaPshot assay for genotyping 44 individual identification single nucleotide polymorphisms," Electrophoresis, Feb. 2011, 32(3-4):368-78.

MacKay, David J.C., "Information theory, inference, and learning algorithms," Aug. 25, 2004, Cambridge University Press, 640 pages.

Single Nucleotide Polymorphisms: Methods and Protocols, 1st ed., Kwok (ed)., 2003, 111-128, 17 pages.

Meyer et al., "Parallel donor genotyping for 46 selected blood group and 4 human platelet antigens using high-throughput MALDI-TOF mass spectrometry," Molecular Typing of Blood Cell Antigens, 2015, 1310:51-70.

Nakorchevsky et al., "Detection of low level mixed Chimerism using high throughput SNP genotyping," J Blood Dis Transfus, Jan. 2016, 7(1):340.

Nomura et al., "Proteome-based bacterial identification using matrix-assisted laser desorption ionization—time of flight mass spectrometry (MALDI-TOF MS): A revolutionary shift in clinical diagnostic microbiology," Biochimica et Biophysica Acta (BBA)—Proteins and Proteomics, Jun. 2015, 1854(6):528-37.

Noshi et al., "Isozymes of," ALPHA, -amylase in human urine the Journal of Biochemistry, 1975, 77(1):163-9.

Oliveira et al., "Human urine as a noninvasive source of kidney cells," Stem cells international, Dec. 3, 2014, 2015(1):362562, 7 pages.

Olivier et al., "The Invader® assay for SNP genotyping," Mutation research/fundamental and molecular mechanisms of mutagenesis, Jun. 3, 2005, 573(1-2):103-10.

Onofri et al., "Development of multiplex PCRs for evolutionary and forensic applications of 37 human Y chromosome SNPs," Forensic science international, Feb. 10, 2006, 157(1):23-35.

Ota et al., "Single nucleotide polymorphism detection by polymerase chain reaction-restriction fragment length polymorphism," Nature protocols, Nov. 2007, 2(11):2857-64.

Peters et al., "Accurate whole-genome sequencing and haplotyping from 10 to 20 human cells," Nature, Jul. 12, 2012, 487(7406):190-5.

Prinz et al., "DNA typing of urine samples following several years of storage," International Journal of Legal Medicine, Mar. 1993, 106:75-9.

Rahi et al., "Matrix-assisted laser desorption/ionization time-of-flight mass-spectrometry (MALDI-TOF MS) based microbial identifications: challenges and scopes for microbial ecologists," Frontiers in Microbiology, Aug. 30, 2016, 7:1359.

Sethu et al., "Microfluidic isolation of leukocytes from whole blood for phenotype and gene expression analysis," Analytical chemistry, Aug. 2006, 78(15):5453-61.

(56) References Cited

OTHER PUBLICATIONS

Shlens, "A tutorial on principal component analysis," CoRR, Submitted on Apr. 3, 2014, arXiv:1404.1100, 12 pages.

Shuber et al., "A simplified procedure for developing multiplex PCRs," Genome Research, Dec. 1995, 5(5):488-93.

Simpson et al., "Drug abuse treatment process components that improve retention," Journal of substance abuse treatment, Nov. 1997, 14(6):565-72.

Singhal et al., "MALDI-TOF mass spectrometry: an emerging technology for microbial identification and diagnosis," Frontiers in microbiology, Aug. 5, 2015, 6:791.

Smith, "A tutorial on principal components analysis," Feb. 26, 2002, Cornell University, USA, 27 pages.

Soukos et al., "A rapid method to detect dried saliva stains swabbed from human skin using fluorescence spectroscopy," Forensic science international, Dec. 11, 2000, 114(3):133-8.

Storm et al., "MALDI-TOF mass spectrometry-based SNP genotyping," Single nucleotide polymorphisms: methods and protocols, 2003, 212:241-62, 22 pages.

Tahira et al., "dbQSNP: A database of SNPs in human promoter regions with allele frequency information determined by single-strand conformation polymorphism-based methods," Human mutation, Aug. 2005, 26(2):69-77.

The International SNP Map Working Group, "A map of human genome sequence variation containing 1.42 million single nucleotide polymorphisms," Nature, 2001, 409:928-933.

The International SNP Map Working Group, A map of human genome sequence variation containing 1.42 million single nucleotide polymorphisms Nature, Feb. 15, 2001, 409(6822):928-33.

Wang et al., "Critical factors determining the quantification capability of matrix-assisted laser desorption/ionization-time-of-flight mass spectrometry," Philosophical Transactions of the Royal Society A: Mathematical, Physical and Engineering Sciences, Oct. 28, 2016, 374(2079):20150371, 14 pages.

Wang et al., "Normalization regarding non-random missing values in high-throughput mass spectrometry data," Biocomputing, Sep. 23, 2005, 12(14):315-326, 13 pages.

Wittwer et al., "High-resolution genotyping by amplicon melting analysis using LCGreen," Clinical chemistry, Jun. 2003, 49(6):853-60.

Woodward et al., "Bi-allelic SNP genotyping using the TaqMan® assay," Crop Breeding: Methods and Protocols, 2014:67-74.

Yu et al., "Denaturing high performance liquid chromatography: high throughput mutation screening in familial hypertrophic cardiomyopathy and SNP genotyping in motor neurone disease," Journal of clinical pathology, May 2005, 58(5):479-85.

Zhang et al., "A novel multiplex tetra-primer ARMS-PCR for the simultaneous genotyping of six single nucleotide polymorphisms associated with female cancers," PloS one, Apr. 17, 2013, 8(4):e62126, 8 pages.

* cited by examiner

METHODS OF CHARACTERIZING A URINE SAMPLE

CROSS-REFERENCE TO RELATED APPLICATION

This application is a continuation of U.S. patent application Ser. No. 17/391,876, filed on Aug. 2, 2021, which is a continuation of U.S. patent application Ser. No. 16/564,170, filed on Sep. 9, 2019 (now U.S. Pat. No. 11,079,320), which a continuation of U.S. patent application Ser. No. 15/730, 433, filed on Oct. 11, 2017 (now U.S. Pat. No. 10,451,544), which claims benefit to U.S. Provisional Patent Application Ser. No. 62/406,692, filed on Oct. 11, 2016, the contents of which are incorporated by reference in their entirety.

SEQUENCE LISTING

This application contains a Sequence Listing that has been submitted electronically as an XML file named 39930-0003004_SL_ST26.xml. The XML file, created on Apr. 1, 2024, is 4,144 bytes in size. The material in the XML file is hereby incorporated by reference in its entirety.

TECHNICAL FIELD

This disclosure relates to methods of urine testing.

BACKGROUND

Urine drug testing is a commonly used tool to detect a subject's use of drugs, both legal (e.g., controlled substances) and illegal. During the last half century the use of urine drug testing has been used throughout the military, in the public and private workplace, in courts, and in medical clinics and care centers. The urine drug tests are used primarily to detect illegal or banned substances in a subject's system. In the clinical setting, physicians test their patients to determine if their patients are adhering to their prescriptions. Urine drug testing has become a routinely used effective tool in the assessment and ongoing management of patients who are treated with controlled substances for, e.g., chronic pain. The urine drug testing results provide confirmation of the agreed-upon treatment plan and diagnose relapse or drug abuse.

The results of a urine drug test can have serious consequences for a patient including termination of prescription. In fear of the possible consequences, patients have developed a variety of methods to cheat by substituting their own urine sample with synthetic or chemically-adulterated urines. Patients who "cheat" a urine drug test by using chemically-adulterated samples or synthetic urine present a problem for the health care because the ongoing care plan will not be based on accurate information. Currently, the best method for validating that a patient's sample is in fact their own is by observation during sample collection—which is not always possible.

SUMMARY

The present invention focuses on methods developed to characterize a urine sample from a subject (e.g., used in association with drug testing or to achieve quality control). In view of this discovery, provided herein are methods of characterizing a urine sample that include: (a) providing a urine sample from a subject, determining one or more of the light absorption, luminescence, phosphorescence, fluorescence, and chemiluminescence of the urine sample at two or more wavelengths of light; (c) applying one or more eigenvectors derived from a principle component algorithm to a standardized dataset derived from the determined light absorption, luminescence, phophophorescence, fluorescence, and chemiluminescence of the urine sample to generate a Urine Characterization Index (UCI) including one or more values for corresponding principle component(s); and (d) charactering a urine sample as a natural urine sample, a lyophilized urine sample, a diluted natural urine sample, a synthetic urine sample, or a chemically-adulterated urine sample based on the UCI. Also provided are methods of characterizing a urine sample from a subject that include: (a) providing a urine sample collected from a subject; determining the absence at a first wavelength (A1) and the absorbance at a second wavelength (A2) of the urine sample, where the first wavelength is from about 230 nm to about 250 nm, and the second wavelength is from about 260 nm to 340 nm; (c) applying an algorithm to the determined A1 and the determined A2 to generate a Urine Characterization Score (UCS), where the algorithm includes a ratio of the determined A1 to the determined A2; and (d) characterizing a urine sample as a natural urine sample, a chemically-adulterated urine sample, a lyophilized urine sample, a diluted natural urine sample, or a synthetic urine sample based on the UCS.

Provided herein are methods of characterizing a urine sample from a subject that include: (a) providing a urine sample from a subject; (b) determining one or more (e.g., two, three, four, or five) of the light absorption, luminescence, phosphorescence, fluorescence, and chemiluminescence of the urine sample at two or more wavelengths of light; (c) applying one or more eigenvectors derived from a principle component algorithm to a standardized dataset derived from the determined light absorption, luminescence, phosphorescence, fluorescence, and chemiluminescence of the urine sample to generate a Urine Characterization Index (UCI) including one or more values for corresponding principle component(s); and (d) characterizing a urine sample as a natural urine sample, a lyophilized urine sample, a diluted natural urine sample, a synthetic urine sample, or a chemically-adulterated urine sample based on the UCI. In some embodiments of these methods, the chemically-adulterated urine is a surfactant-adulterated urine. In some embodiments of these methods, step (b) includes determining the light absorption of the urine sample. In some embodiments of these methods, step (b) includes determining the light absorption of one or more of ultraviolet light wavelength(s), visible light wavelength(s), near-infrared light wavelength(s), and infrared absorption light wavelengths. In some embodiments of these methods, step (b) includes determining the light absorption of the urine sample at wavelengths of about 200 nm to about 1000 nm. In some embodiments of these methods, step (b) includes determining the light absorption of the urine sample at wavelengths of about 200 nm to about 340 nm.

In some embodiments of these methods, step (c) includes applying an eigenvector derived from the principle component algorithm to a dataset derived from the determined light absorption to generate a value for one principle component. In some embodiments of these methods, step (c) includes applying two eigenvectors derived from the principle component algorithm to a dataset derived from the determined light absorption, luminescence, phosphorescence, fluorescence, chemiluminescence, or bioluminescence to generate values in two-dimensional principle component space. In some embodiments of these methods, step (c) includes applying two eigenvectors derived from the principle component algorithm to a dataset derived from the determined light absorption to generate values in two-dimensional principle component space. In some embodiments of these methods, step (c) includes applying three eigenvectors derived from the principle component algorithm to a dataset derived from the determined light absorption, luminescence, phosphorescence, fluorescence, chemiluminescence, or bioluminescence to generate values in three-dimensional principle component space. In some embodiments of these methods, step (c) includes applying three eigenvectors derived from the principle component algorithm to a dataset derived from the determined light absorption to generate values in three-dimensional principle component space. In some embodiments of these methods, step (c) includes applying four eigenvectors derived from the principle component algorithm to a dataset derived from the determined light absorption, luminescence, phosphorescence, fluorescence, chemiluminescence, or bioluminescence to generate values in four-dimensional principle component space. In some embodiments of these methods, step (c) includes applying four eigenvectors derived from the principle component algorithm to a dataset derived from the determined light absorption to generate values in four-dimensional principle component space.

In some embodiments of these methods, step (d) includes characterizing a urine sample through the use of a clustering algorithm. In some embodiments of these methods, the clustering algorithm is a hierarchical clustering algorithm, a k-means clustering algorithm, or a statistical distribution model. In some embodiments of these methods, step (d) includes characterizing a urine sample by performing regression analysis on the values of principle components. In some embodiments of these methods, step (d) includes comparing the UCI of the sample to a UCI of a natural urine sample, a chemically-adulterated urine sample, a lyophilized urine sample, a diluted natural urine sample, or a synthetic urine sample.

Also provided herein are methods of characterizing a urine sample from a subject that include: (a) providing a urine sample collected from a subject; (b) determining the absorbance at a first wavelength (A1) and the absorbance at a second wavelength (A2) of the urine sample, where the first wavelength is from about 230 nm to 250 nm, and the second wavelength is from about 260 nm to 340 nm; (c) applying an algorithm to the determined A1 and the determined A2 to generate a Urine Characterization Score (UCS), where the algorithm includes a ratio of the determined A1 to the determined A2; and (d) characterizing a urine sample as a natural urine sample, a chemically-adulterated urine sample, a lyophilized urine sample, a diluted natural urine sample, or a synthetic urine sample based on the UCS. In some embodiments of these methods, the UCS is generated using the Formula (XI): UCS=A1/A2. In some embodiments of these methods, the UCS is generated using the Formula (XII): UCS=10×log(A1/A2). In some embodiments of these methods, the first wavelength is 240 nm and the second wavelength is 280 nm. In some embodiments of these methods, step (d) includes charactering the urine sample as a synthetic urine sample if UCS is greater than 0.8. In some embodiments of these methods, step (d) includes characterizing the urine sample as a synthetic urine sample if the UCS is less than 0.25.

In some embodiments of any of the methods described herein, the urine sample is characterized as a natural urine sample and the method further includes: (e) performing an assay to determine the level of one or more drug metabolites in the urine sample. Some embodiments of these methods further include: (f) identifying a subject having an elevated level of one or more drug metabolites in the urine sample as compared to a reference level of the one or more drug metabolites, where the drug metabolites are metabolites of an illegal or controlled substance; and (g) admitting the subject into a drug dependency program, ceasing administration of the controlled substance to the subject, or reducing the dose and/or frequency of administration of the controlled substance to the subject. In some embodiments of these methods, the drug dependency program includes administering to the subject in step (g) a drug replacement therapy.

Some embodiments of any of the methods described herein further include: (e) selecting a subject having a urine sample characterized in step (d) as a surfactant-adulterated urine sample; and (f) obtaining an additional urine sample from the selected subject. Some embodiments of any of the methods described herein further include: (e) selecting a subject having a urine sample characterized in step (d) as a lyophilized urine sample; and (f) obtaining an additional urine sample from the selected subject. Some embodiments of any of the methods described herein further include: (e) selecting a subject having a urine sample characterized in step (d) as a diluted natural urine sample; and (f) obtaining an additional urine sample from the selected subject. Some embodiments of any of the methods described herein further include: (e) selecting a subject having a urine sample characterized in step (d) as a synthetic urine sample; and (f) obtaining an additional urine sample from the selected subject.

In some embodiments of any of the methods described herein, the additional urine sample is obtained through a witnessed urine test. Some embodiments of any of the methods described herein further include: (g) performing an assay to determine the level of one or more drug metabolites in the additional urine sample. Some embodiments of any of the methods described herein further include: (h) identifying a subject having an elevated level of one or more drug metabolites in the additional urine sample as compared to a reference level of the one or more drug metabolites, where the drug metabolites are metabolites of an illegal or controlled substance; and (i) admitting the subject into a drug dependency program, ceasing administration of the controlled substance to the subject, or reducing the dose and/or frequency of administration of the controlled substance to the subject. In some embodiments of any of the methods described herein, the drug dependency program includes administering to the subject in step (i) a drug replacement therapy.

Some embodiments of any of the methods described herein further include: (e) selecting a subject having a urine sample characterized in step (d) as a surfactant-adulterated urine sample; (f) obtaining a sample including blood, serum, hair, or plasma from the subject; and (g) performing an assay to determine the level of one or more drug metabolites in the sample from step (f). Some embodiments of any of the methods described herein further include: (e) selecting a subject having a urine sample characterized in step (d) as a lyophilized urine sample; (f) obtaining a sample including blood, serum, hair, or plasma from the subject; and (g) performing an assay to determine the level of one or more drug metabolites in the sample from step (f). Some embodiments of any of the methods described herein further include: (e) selecting a subject having a urine sample characterized in step (d) as a diluted natural urine sample; (f) obtaining a sample including blood, serum, hair, or plasma from the subject; and (g) performing an assay to determine the level of one or more drug metabolites in the sample from step (f). Some embodiments of any of the methods provided herein further include: (e) selecting a subject having a urine sample characterized in step (d) as a synthetic urine sample; (f) obtaining a sample including blood, serum, hair, or plasma from the subject; and (g) performing an assay to determine the level of one or more drug metabolites in the sample from step (f). Some embodiments of any of the methods described herein further include: (h) identifying a subject having an elevated level of one or more drug metabolites in the sample from step (f) as compared to a reference level of the one or more drug metabolites, where the drug metabolites are metabolites of an illegal or controlled substance; and (i) admitting the subject into a drug dependency program, ceasing administration of the controlled substance to the subject, or reducing the dose or frequency of administration of the controlled substance to the subject. In some embodiments of any of the methods described herein, the drug dependency program includes administering to the subject in step (i) a drug replacement therapy.

Some embodiments of any of the methods described herein further include recording the characterization of the urine sample in the subject's medical record. In some embodiments of any of the methods described herein, the subject's medical record is a computer readable medium. Some embodiments of any of the methods described herein further include notifying the subject's insurance provider, employer, or potential future employer of the characterization of the urine sample. Some embodiments of any of the methods described herein further include notifying a pharmacist or a medical professional of the characterization of the urine sample.

In some embodiments of any of the methods described herein, the subject has not been diagnosed as having an illegal or controlled substance addiction. In some embodiments of any of the methods described herein, the subject has been identified as having an illegal or controlled substance addiction. In some embodiments of any of the methods described herein, the subject is being treated on an outpatient basis for an illegal or controlled substance addiction.

In some embodiments of any of the methods described herein, the determining in step (b) is performed using high throughput processing. Some embodiments of any of the methods described herein further include amplifying and sequencing nucleic acid present in the urine sample. Some embodiments of any of the methods described herein further include detecting one or more of statherin, alpha-amylase, lingual lipase, and lysozyme in the urine sample.

As used herein, the word "a" before a noun represents one or more of the particular noun. For example, the phrase "a urine sample" represents "one or more urine samples."

The term "subject" means a vertebrate, including any member of the class mammalia, including humans, sports or pet animals, such as horse (e.g., race horse) or dog (e.g., race dogs), and higher primates. In preferred embodiments, the subject is a human.

The term "natural urine sample" is a urine produced by the body of a mammal (e.g., human).

The term "lyophilized urine sample" is a natural urine sample that has been lyophilized and reconstituted in a fluid (e.g., an aqueous solution, e.g., water).

The term "diluted natural urine sample" is a natural urine sample that has been diluted with a fluid (e.g., an aqueous solution, e.g., water) that is not a natural urine sample.

The term "synthetic urine sample" is art known and means a synthetic liquid that is not produced by the body of a mammal (e.g., human) that is meant to substitute for urine produced by the body of a mammal (e.g., a human). As is known in the art, synthetic urine is commercially available from a number of vendors. As is known in the art, synthetic urine typically contains nitrogenous waste products of synthetic origin (e.g., urea, creatinine, and/or uric acid), and inorganic salts including, e.g., potassium chloride, calcium chloride, sodium chloride, magnesium chloride, calcium chloride, sodium sulfate, ammonium diphosphate, potassium diphosphate, sodium phosphate, and/or sodium diphosphate. Synthetic urine is also known, on occasion, to be fortified with, e.g., preservative agents (e.g., sodium azide), hormones (e.g., estrogen), and/or coloring agents (e.g., synthetic dyes, B vitamins, and/or natural pigments (e.g., β-carotene)).

The term "chemically-adulterated urine sample" is a natural urine sample that has been contacted with a chemical substance to alter one or more biophysical properties of the natural urine sample. For example, a chemically-adulterated urine sample can be contacted with a chemical substance that alters the absorbance of the natural urine sample at one or more wavelengths of light. For example, a chemically-adulterated urine sample can be contacted with a surfactant to alter one or more biophysical properties of the natural urine sample.

As used herein, the term "principal component analysis" or "principal component algorithm" refers to a statistical method that uses an orthogonal transformation to convert a set of two or more observations of two or more possibly correlated variables into a set of two or more values of linearly uncorrelated variables called principal components. Principle component analysis finds the two or more principal components of the dataset and transforms the data into a new, lower-dimensional subspace. The first principle component, which can be represented by an eigenvector, mathematically corresponds to a direction in the original n-dimensional space, so that the first principal component accounts for as much of the variance in the data as possible, and each succeeding principle component accounts for as much of the remaining variance as possible.

As used herein, the term "principal component space" refers to a subspace in which the original data (e.g., one or more of the light absorption, luminescence, phosphorescence, fluorescence, and chemiluminescence of a urine sample at two or more wavelengths of light) has been transformed into.

As used herein, the term "eigenvector" refers to a vector which, when acted on by a particular linear transformation, produces a scalar multiple of the original vector. The scalar in question refers to an eigenvalue corresponding to a particular eigenvector.

The term "drug metabolite" is art known and means a break-down product of a controlled or illegal substance produced by a mammal's body following administration of the controlled or illegal substance to the mammal (e.g., human). A wide variety of drugs, drug metabolites, and assays for detecting the levels of drugs and drug metabolites are known in the art. Non-limiting examples of drugs, drug metabolites, and vendors that sell kits for determining the level of one or more drugs and drug metabolites are described herein.

The term "potential future employer" means a person or business entity that is considering a subject for employment and that requires or asks employment candidates to provide a urine sample for testing as part of the job application process. For example, a potential future employer can be a state or federal government, a medical care facility (e.g., a clinic or a hospital), a transportation company, or an airline company.

The term "controlled substance" means an agent or material that is regulated by a government (e.g., state, federal government, or a governmental drug regulatory agency, such as the U.S. Food and Drug Administration), but its administration to at least some persons is not illegal. For example, the dosage and frequency of administration of a controlled substance can be regulated by a government. In some examples, certain persons in a population are warned not to consume a controlled substance. Non-limiting examples of controlled substances are prescription drugs and marijuana.

The term "drug replacement therapy" means administration of an agent that mimics the pharmacological effect of a controlled or illegal substance but is longer acting, less potent, less toxic, and/or has an improved safety profile than the controlled or illegal substance.

The term "DNA-adulterated sample" means a urine sample (e.g., synthetic urine sample) from a subject that has been manipulated to add genomic DNA from the subject, where the added genomic DNA is from a source other than mammalian cells present in urine.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
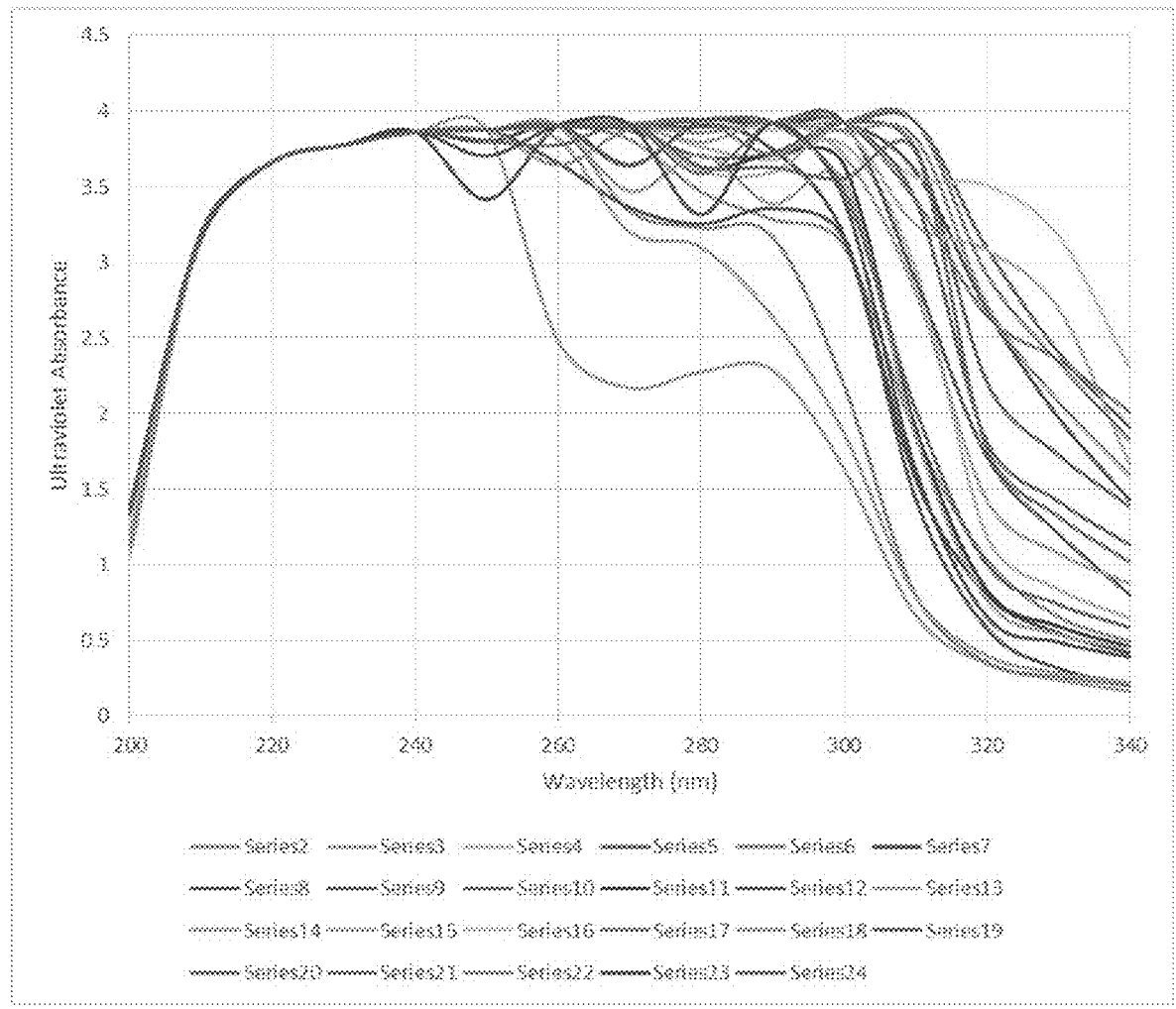
FIG. 1 is a graph showing absorbance spectra of natural urine samples. The absorbance characteristics can be described qualitatively as strong absorbance throughout the ultraviolet region, particularly at wavelengths centered on 240 nm, 280 nm, and 300 nm.

This disclosure relates to methods of characterizing a urine sample from a subject. Non-limiting aspects of these methods are described below. As can be appreciated in the art, the various aspects described below can be used in any combination without limitation.

Subjects

In any of the methods described herein, a subject may be either a human or a non-human animal. In some embodiments, the subject has not been diagnosed as having an illegal or controlled substance addiction. In some embodiments of any of the methods described herein, the subject has been identified as having an illegal or controlled substance addiction (e.g., a subject that has already undergone treatment (e.g., successful or unsuccessful treatment) for his or her illegal or controlled substance addiction). In some embodiments of any of the methods described herein, the subject is being treated on an outpatient basis for an illegal or controlled substance addiction. In some embodiments, the subject is receiving inpatient treatment for his or her illegal or controlled substance addiction.

In some embodiments, the subject is a female (e.g., a pregnant female). In some embodiments, the subject is a male. A subject in any of the methods described herein can be a child, an adolescent, a teenager, or an adult (a subject that greater than 18 years old, e.g., greater than 20 years old, greater than 25 years old, greater than 30 years old, greater than 35 years old, greater than 40 years old, greater than 45 years old, greater than 50 years old, greater than 55 years old, greater than 60 years old, greater than 65 years old, greater than 70 years old, greater than 75 years old, greater than 80 years old, greater than 90 years old, or greater than 100 years old). In any of the methods described herein, the subject may employed by the military, may be a truck driver, a train engineer, a pilot, a medical professional (e.g., a physician, nurse, nurse's assistant, or a physician's assistant), or a pharmacist. In any of the methods described herein, the subject has a family history of illegal or controlled substance addiction. In any of the methods described herein, the subject can be identified as previously submitting a synthetic urine sample, a diluted natural urine sample, a urine sample originating from another subject, a lyophilized urine sample, a chemically-adulterated urine sample, or an adulterated urine sample.

Urine Samples

Some embodiments of the methods described herein can include a step of providing a urine sample collected from a subject. In some examples, the methods described herein can further include a step of obtaining a urine sample from a subject. A urine sample is typically obtained using unwitnessed urine sample collection. As described herein, a urine sample can be a natural urine sample, a synthetic urine sample, a chemically-adulterated urine sample, a lyophilized urine sample, or a diluted natural urine sample, or any mixture thereof.

A urine sample can have a volume of at least 1 mL (e.g., at least 2 mL, at least 3 mL, at least 4 mL, at least 5 mL, at least 6 mL, at least 7 mL, at least 8 mL, at least 9 mL, at least 10 mL, at least 12 mL, at least 14 mL, at least 16 mL, at least 18 mL, at least 20 mL, at least 22 mL, at least 24 mL, at least 26 mL, at least 28 mL, or at least 30 mL). For example, a urine sample can have a volume of between about 1 mL and about 30 mL, between about 5 mL and about 30 mL, between about 10 mL and about 30 mL, or between about 15 mL and about 30 mL.

In some examples of any of the methods described herein, the urine sample can be stored, e.g., for at least 1 hour (e.g., at least 6 hours, at least 12 hours, at least 1 day, at least 2 days, at least 3 days, at least 4 days, at least 5 days, at least 6 days, or at least 7 days) at a temperature below 25° C. (e.g., at about 15° C., at about 10° C., at about 4° C., at about 0° C., at about −20° C., at about −40° C., at about −80° C., at about −86° C., or at about −196° C.) before any of the present methods are performed on the urine sample. In some embodiments, the urine sample can be centrifuged or clarified (e.g., by gravity) before any of the present methods are performed. In some embodiments, the urine sample can be filtered (e.g., to remove any mammalian cells, bacterial cells, yeast cells, or soluble or insoluble protein aggregates) before any of the present methods are performed.

A natural urine sample may include the presence of one or more of cellular material including intact cells, components of cellular systems, or cellular debris originating from the mammal providing the specimen, or originating from the growth of prokaryotic lifeforms including any bacterial cells or archaea, or originating from the growth of eukaryotic lifeforms including protists, fungi, or animals found to be in urine from either infection, parasitic growth, or contamination with living organisms after collection. Biological properties of a natural urine sample may also include the presence of enzymatic activity arising from freely soluble enzymes in a natural urine sample, or membrane-bound enzyme(s) adhered or imbedded to cells or cellular debris arising from either prokaryotic or eukaryotic origin. The biological properties of a natural urine sample may also include the presence or evidence of genetic material including DNA or RNA arising from prokaryotic, eukaryotic, or viral origins or the presence or evidence of genetic processes including but not limited to the replication of nucleic acids, DNA cleavage, DNA damage, DNA methylation, DNA repair, gene expression, gene regulation, mutagenesis, nucleic acid denaturation, recombination, RNA cleavage, and viral integration.

The chemical composition of a natural urine sample may also include one or more of the presence or concentration of 1-aliphatic acyclic compounds, aliphatic heteromonocyclic compounds, aliphatic heteropolycyclic compounds, aliphatic homomonocyclic compounds, aliphatic homopolycyclic compounds, alkaloids, and derivatives, amino acids, peptides and analogues, aromatic heteromonocyclic compounds, aromatic heteropolycyclic compounds, aromatic homomonocyclic compounds, aromatic homopolycyclic compounds, carbohydrates and carbohydrate conjugates, homogenous metal compounds, homogenous non-metal compounds, inorganic compounds, lignans and norlignans, lipids, mixed metal/non-metal compounds, nucleosides, nucleotides and analogs, organic acids and derivatives, organic halides, organometallic compounds, organophosphorous compounds, polyketides, tannins, bile acids, degradation or chemical-reaction, or enzymatic-reaction products of any of the above, or other compounds both endogenous and xenobiotic in a natural urine sample occurring due to metabolic processes or otherwise found to occur in a urine sample.

Lyophilized urine samples, diluted natural urine samples, synthetic urine samples, and chemically-adulterated urine samples do not have the same biological properties and/or chemical composition as a natural urine sample, and manipulation of a natural urine sample (e.g., dilution, chemical-adulteration, and lyophilization) can change the characteristics of a natural urine sample. The methods described herein can detect the differences in the biological properties and/or chemical composition between a natural urine sample and a synthetic urine sample, a chemically-adulterated urine sample, a lyophilized urine sample, and a diluted natural urine sample, and can be used to accurately characterize a urine sample as a natural urine sample, a synthetic urine sample, a chemically-altered urine sample, a lyophilized urine sample, or a diluted natural urine sample.

Methods of Characterizing a Urine Sample from a Subject that Include Determining a Urine Characterization Score Provided are methods of characterizing a urine sample from a subject that include: (a) providing a urine sample from a subject; (b) determining the absorbance at a first wavelength (A1) and the absorbance at a second wavelength (A2) of the urine sample, where the A1 is from about 230 nm to about 250 nm (inclusive), and the A2 is from about 260 nm to about 340 nm (inclusive); (c) applying an algorithm to the determined A1 and the determined A2 to generate a UCS, where the algorithm includes a ratio of the determined A1 to the determined A2; and (d) characterizing a urine sample as a natural urine sample, a DNA-adulterated urine sample, a lyophilized urine sample, a diluted natural urine sample, or a synthetic urine sample based on the UCS. Also provided are methods of characterizing a urine sample from a subject that include: (a) determining the absorbance at a first wavelength (A1) and the absorbance at a second wavelength (A2) of a urine sample from a subject, where the A1 is from about 230 nm to about 250 nm (inclusive), and the A2 is from about 260 nm to about 340 nm (inclusive); (b) applying an algorithm to the determined A1 and the determined A2 to generate a UCS, where the algorithm includes a ratio of the determined A1 to the determined A2; and (c) characterizing a urine sample as a natural urine sample, a DNA-adulterated urine sample, a lyophilized urine sample, a diluted natural urine sample, or a synthetic urine sample based on the UCS.

In some embodiments, the A1 is 230 nm, 231 nm, 232 nm, 233 nm, 234 nm, 235 nm, 236 nm, 237 nm, 238 nm, 239 nm, 240 nm, 241 nm, 242 nm, 243 nm, 244 nm, 245 nm, 246 nm, 247 nm, 248 nm, 249 nm, or 250 nm. In some embodiments, the A1 is about 230 nm to about 250 nm, about 249 nm, about 248 nm, about 247 nm, about 246 nm, about 245 nm, about 244 nm, about 243 nm, about 242 nm, about 241 nm, about 240 nm, about 239 nm, about 238 nm, about 237 nm, about 236 nm, about 235 nm, about 234 nm, about 233 nm, or about 232 nm (inclusive); about 231 nm to about 250 nm, about 249 nm, about 248 nm, about 247 nm, about 246 nm, about 245 nm, about 244 nm, about 243 nm, about 242 nm, about 241 nm, about 240 nm, about 239 nm, about 238 nm, about 237 nm, about 236 nm, about 235 nm, about 234 nm, or about 233 nm (inclusive); about 232 nm to about 250 nm, about 249 nm, about 248 nm, about 247 nm, about 246 nm, about 245 nm, about 244 nm, about 243 nm, about 242 nm, about 241 nm, about 240 nm, about 239 nm, about 238 nm, about 237 nm, about 236 nm, about 235 nm, or about 234 nm (inclusive); about 233 nm to about 250 nm, about 249 nm, about 248 nm, about 247 nm, about 246 nm, about 245 nm, about 244 nm, about 243 nm, about 242 nm, about 241 nm, about 240 nm, about 239 nm, about 238 nm, about 237 nm, about 236 nm, or about 235 nm (inclusive); about 234 nm to about 250 nm, about 249 nm, about 248 nm, about 247 nm, about 246 nm, about 245 nm, about 244 nm, about 243 nm, about 242 nm, about 241 nm, about 240 nm, about 239 nm, about 238 nm, about 237 nm, or about 236 nm (inclusive); about 235 nm to about 250 nm, about 249 nm, about 248 nm, about 247 nm, about 246 nm, about 245 nm, about 244 nm, about 243 nm, about 242 nm, about 241 nm, about 240 nm, about 239 nm, about 238 nm, or about 237 nm (inclusive); about 236 nm to about 250 nm, about 249 nm, about 248 nm, about 247 nm, about 246 nm, about 245 nm, about 244 nm, about 243 nm, about 242 nm, about 241 nm, about 240 nm, about 239 nm, or about 238 nm (inclusive); about 237 nm to about 250 nm, about 249 nm, about 248 nm, about 247 nm, about 246 nm, about 245 nm, about 244 nm, about 243 nm, about 242 nm, about 241 nm, about 240 nm, or about 239 nm (inclusive); about 238 nm to about 250 nm, about 249 nm, about 248 nm, about 247 nm, about 246 nm, about 245 nm, about 244 nm, about 243 nm, about 242 nm, about 241 nm, or about 240 nm (inclusive); about 239 nm to about 250 nm, about 249 nm, about 248 nm, about 247 nm, about 246 nm, about 245 nm, about 244 nm, about 243 nm, about 242 nm, or about 241 nm (inclusive); about 240 nm to about 250 nm, about 249 nm, about 248 nm, about 247 nm, about 246 nm, about 245 nm, about 244 nm, about 243 nm, or about 242 nm (inclusive); about 241 nm to about 250 nm, about 249 nm, about 248 nm, about 247 nm, about 246 nm, about 245 nm, about 244 nm, or about 243 nm (inclusive); about 242 nm to about 250 nm, about 249 nm, about 248 nm, about 247 nm, about 246 nm, about 245 nm, or about 244 nm (inclusive); about 243 nm to about 250 nm, about 249 nm, about 248 nm, about 247 nm, about 246 nm, or about 245 nm (inclusive); about 244 nm to about 250 nm, about 249 nm, about 248 nm, about 247 nm, or about 246 nm (inclusive); about 245 nm to about 250 nm, about 249 nm, about 248 nm, or about 247 nm (inclusive); about 246 nm to about 250 nm, about 249 nm, or about 248 nm (inclusive); about 247 nm to about 250 nm or about 249 nm (inclusive); or about 248 nm to about 250 nm (inclusive).

In some embodiments of these methods, the A2 is 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm, 281 nm, 282 nm, 283 nm, 284 nm, 285 nm, 286 nm, 287 nm, 288 nm, 289 nm, 290 nm, 291 nm, 292 nm, 293 nm, 294 nm, 295 nm, 296 nm, 297 nm, 298 nm, 299 nm, 300 nm, 301 nm, 302 nm, 303 nm, 304 nm, 305 nm, 306 nm, 307 nm, 308 nm, 309 nm, 310 nm, 311 nm, 312 nm, 313 nm, 314 nm, 315 nm, 316 nm, 317 nm, 318 nm, 319 nm, 320 nm, 321 nm, 322 nm, 323 nm, 324 nm, 325 nm, 326 nm, 327 nm, 328 nm, 329 nm, 330 nm, 331 nm, 332 nm, 333 nm 334 nm, 335 nm, 336 nm, 337 nm, 338 nm, 339 nm, or 340 nm. In some embodiments of these methods, A2 is about 260 nm to about 340 nm, about 335 nm, about 330 nm, about 325 nm, about 320 nm, about 315 nm, about 310 nm, about 305 nm, about 300 nm, about 295 nm, about 290 nm, about 285 nm, about 280 nm, about 275 nm, about 270 nm, or about 265 nm (inclusive); about 265 nm to about 340 nm, about 335 nm, about 330 nm, about 325 nm, about 320 nm, about 315 nm, about 310 nm, about 305 nm, about 300 nm, about 295 nm, about 290 nm, about 285 nm, about 280 nm, about 275 nm, or about 270 nm (inclusive); about 270 nm to about 340 nm, about 335 nm, about 330 nm, about 325 nm, about 320 nm, about 315 nm, about 310 nm, about 305 nm, about 300 nm, about 295 nm, about 290 nm, about 285 nm, about 280 nm, or about 275 nm (inclusive); about 275 nm to about 340 nm, about 335 nm, about 330 nm, about 325 nm, about 320 nm, about 315 nm, about 310 nm, about 305 nm, about 300 nm, about 295 nm, about 290 nm, about 285 nm, about 280 nm, about 275 nm, or about 270 nm (inclusive); about 270 nm to about 340 nm, about 335 nm, about 330 nm, about 325 nm, about 320 nm, about 315 nm, about 310 nm, about 305 nm, about 300 nm, about 295 nm, about 290 nm, about 285 nm, or about 280 nm (inclusive); about 280 nm to about 340 nm, about 335 nm, about 330 nm, about 325 nm, about 320 nm, about 315 nm, about 310 nm, about 305 nm, about 300 nm, about 295 nm, about 290 nm, about 285 nm, about 280 nm, about 275 nm, or about 270 nm (inclusive); about 270 nm to about 340 nm, about 335 nm, about 330 nm, about 325 nm, about 320 nm, about 315 nm, about 310 nm, about 305 nm, about 300 nm, about 295 nm, about 290 nm, or about 285 nm (inclusive); about 285 nm to about 340 nm, about 335 nm, about 330 nm, about 325 nm, about 320 nm, about 315 nm, about 310 nm, about 305 nm, about 300 nm, about 295 nm, about 290 nm, about 285 nm, about 280 nm, about 275 nm, or about 270 nm (inclusive); about 270 nm to about 340 nm, about 335 nm, about 330 nm, about 325 nm, about 320 nm, about 315 nm, about 310 nm, about 305 nm, about 300 nm, about 295 nm, or about 290 nm (inclusive); about 290 nm to about 340 nm, about 335 nm, about 330 nm, about 325 nm, about 320 nm, about 315 nm, about 310 nm, about 305 nm, about 300 nm, or about 295 nm (inclusive); about 295 nm to about 340 nm, about 335 nm, about 330 nm, about 325 nm, about 320 nm, about 315 nm, about 310 nm, about 305 nm, or about 300 nm (inclusive); about 300 nm to about 340 nm, about 335 nm, about 330 nm, about 325 nm, about 320 nm, about 315 nm, about 310 nm, or about 305 nm (inclusive); about 305 nm to about 340 nm, about 335 nm, about 330 nm, about 325 nm, about 320 nm, about 315 nm, or about 310 nm (inclusive); about 310 nm to about 340 nm, about 335 nm, about 330 nm, about 325 nm, about 320 nm, or about 315 nm (inclusive); about 315 nm to about 340 nm, about 335 nm, about 330 nm, about 325 nm, or about 320 nm (inclusive); about 320 nm to about 340 nm, about 335 nm, about 330 nm, or about 325 nm (inclusive); about 325 nm to about 340 nm, about 335 nm, or about 330 nm (inclusive); about 330 nm to about 340 nm or about 335 nm (inclusive); or about 335 nm to about 340 nm (inclusive). In some embodiments of any of these methods, the A1 is 240 nm and the A2 is 280 nm.

In some embodiments of these methods, the UCS is generated using the following formula:

$$UCS = A1/A2. \quad \text{(XI)}$$

For Formula XI, if the determined UCS is below than a reference value (e.g., a threshold value), it indicates that the urine sample is a synthetic urine sample. An appropriate reference value (e.g., threshold value) for identifying a synthetic urine sample can be determined by the training dataset (e.g., any of the exemplary training datasets described herein). In some embodiments, a reference value (e.g., threshold value) for identifying a synthetic urine sample is selected because the reference value has the highest accuracy when the reference value is applied to a training dataset (e.g., any of the exemplary training datasets described herein). In some embodiments, a reference value for identifying a synthetic urine sample is selected because the reference value (e.g., threshold value) has the highest area under the curve (AUC) for receiver operating characteristic (ROC) when the reference value is applied to a training dataset (e.g., any of the exemplary training datasets described herein). In some embodiments, the reference value (e.g., threshold value) can be any value from 0.01 to about 0.25, about 0.24, about 0.23, about 0.22, about 0.21, about 0.20, about 0.19, about 0.18, about 0.17, about 0.16, about 0.15, about 0.14, about 0.13, about 0.12, about 0.11, about 0.10, about 0.09, about 0.08, about 0.07, about 0.06, about 0.05, about 0.04, about 0.03, or about 0.02 (inclusive); about 0.02 to about 0.25, about 0.24, about 0.23, about 0.22, about 0.21, about 0.20, about 0.19, about 0.18, about 0.17, about 0.16, about 0.15, about 0.14, about 0.13, about 0.12, about 0.11, about 0.10, about 0.09, about 0.08, about 0.07, about 0.06, about 0.05, about 0.04, or about 0.03 (inclusive); about 0.03 to about 0.25, about 0.24, about 0.23, about 0.22, about 0.21, about 0.20, about 0.19, about 0.18, about 0.17, about 0.16, about 0.15, about 0.14, about 0.13, about 0.12, about 0.11, about 0.10, about 0.09, about 0.08, about 0.07, about 0.06, about 0.05, or about 0.04 (inclusive); about 0.04 to about 0.25, about 0.24, about 0.23, about 0.22, about 0.21, about 0.20, about 0.19, about 0.18, about 0.17, about 0.16, about 0.15, about 0.14, about 0.13, about 0.12, about 0.11, about 0.10, about 0.09, about 0.08, about 0.07, about 0.06, or about 0.05 (inclusive); about 0.05 to about 0.25, about 0.24, about 0.23, about 0.22, about 0.21, about 0.20, about 0.19, about 0.18, about 0.17, about 0.16, about 0.15, about 0.14, about 0.13, about 0.12, about 0.11, about 0.10, about 0.09, about 0.08, about 0.07, or about 0.06 (inclusive); about 0.06 to about 0.25, about 0.24, about 0.23, about 0.22, about 0.21, about 0.20, about 0.19, about 0.18, about 0.17, about 0.16, about 0.15, about 0.14, about 0.13, about 0.12, about 0.11, about 0.10, about 0.09, about 0.08, or about 0.07 (inclusive); about 0.07 to about 0.25, about 0.24, about 0.23, about 0.22, about 0.21, about 0.20, about 0.19, about 0.18, about 0.17, about 0.16, about 0.15, about 0.14, about 0.13, about 0.12, about 0.11, about 0.10, about 0.09, or about 0.08 (inclusive); about 0.08 to about 0.25, about 0.24, about 0.23, about 0.22, about 0.21, about 0.20, about 0.19, about 0.18, about 0.17, about 0.16, about 0.15, about 0.14, about 0.13, about 0.12, about 0.11, about 0.10, or about 0.09 (inclusive); about 0.09 to about 0.25, about 0.24, about 0.23, about 0.22, about 0.21, about 0.20, about 0.19, about 0.18, about 0.17, about 0.16, about 0.15, about 0.14, about 0.13, about 0.12, about 0.11, or about 0.10 (inclusive); about 0.10 to about 0.25, about 0.24, about 0.23, about 0.22, about 0.21, about 0.20, about 0.19, about 0.18, about 0.17, about 0.16, about 0.15, about 0.14, about 0.13, about 0.12, or about 0.11 (inclusive); about 0.11 to about 0.25, about 0.24, about 0.23, about 0.22, about 0.21, about 0.20, about 0.19, about 0.18, about 0.17, about 0.16, about 0.15, about 0.14, about 0.13, or about 0.12 (inclusive); about 0.12 to about 0.25, about 0.24, about 0.23, about 0.22, about 0.21, about 0.20, about 0.19, about 0.18, about 0.17, about 0.16, about 0.15, about 0.14, or about 0.13 (inclusive); about 0.13 to about 0.25, about 0.24, about 0.23, about 0.22, about 0.21, about 0.20, about 0.19, about 0.18, about 0.17, about 0.16, about 0.15, or about 0.14 (inclusive); about 0.14 to about 0.25, about 0.24, about 0.23, about 0.22, about 0.21, about 0.20, about 0.19, about 0.18, about 0.17, about 0.16, or about 0.15 (inclusive); about 0.15 to about 0.25, about 0.24, about 0.23, about 0.22, about 0.21, about 0.20, about 0.19, about 0.18, about 0.17, or about 0.16 (inclusive); about 0.16 to about 0.25, about 0.24, about 0.23, about 0.22, about 0.21, about 0.20, about 0.19, about 0.18, or about 0.17 (inclusive); about 0.17 to about 0.25, about 0.24, about 0.23, about 0.22, about 0.21, about 0.20, about 0.19, or about 0.18 (inclusive); about 0.18 to about 0.25, about 0.24, about 0.23, about 0.22, about 0.21, about 0.20, or about 0.19 (inclusive); about 0.19 to about 0.25, about 0.24, about 0.23, about 0.22, about 0.21, or about 0.20 (inclusive); about 0.20 to about 0.25, about 0.24, about 0.23, about 0.22, or about 0.21 (inclusive); about 0.21 to about 0.25, about 0.24, about 0.23, or about 0.22 (inclusive); about 0.22 to about 0.25, about 0.24, or about 0.23 (inclusive); about 0.23 to about 0.25, or about 0.24 (inclusive); or about 0.24 to about 0.25 (inclusive), when using Formula XI, and a UCS that is below the reference value indicates that the urine sample is a synthetic urine sample. In some embodiments, the reference value can be about 0.25, about 0.24, about 0.23, about 0.22, about 0.21, about 0.20, about 0.19, about 0.18, about 0.17, about 0.16, about 0.15, about 0.14, about 0.13, about 0.12, about 0.11, about 0.10, about 0.09, about 0.08, about 0.07, about 0.06, about 0.05, about 0.04, about 0.03, about 0.02, or about 0.01, when using Formula XI, and a UCS that is below the reference value indicates that the urine sample is a synthetic urine sample.

For Formula XI, if the determined UCS is above a reference value (e.g., a threshold value), it indicates that the urine sample is a natural urine sample. As described above, an appropriate reference value (e.g., threshold value) for identifying a natural urine sample can be determined by the training dataset (e.g., any of the exemplary training datasets described herein). In some embodiments, a reference value (e.g., threshold value) for identifying a natural urine sample can be selected because the reference value has the highest accuracy when the reference value is applied to a training dataset (e.g., any of the exemplary training datasets described herein). In some embodiments, a reference value for identifying a natural urine sample is selected because the reference value (e.g., threshold value) has the highest area under the curve (AUC) for receiver operating characteristic (ROC) when the reference value is applied to a training dataset (e.g., any of the exemplary training datasets described herein). In some embodiments, the reference value (e.g., threshold value) can be any value from, e.g., about 0.8 to about 2.0, about 1.95, about 1.9, about 1.85, about 1.8, about 1.75, about 1.7, about 1.65, about 1.6, about 1.55, about 1.5, about 1.45, about 1.4, about 1.35, about 1.3, about 1.25, about 1.2, about 1.15, about 1.1, about 1.05, about 1.0, about 0.95, about 0.9, or about 0.85 (inclusive); about 0.85 to about 2.0, about 1.95, about 1.9, about 1.85, about 1.8, about 1.75, about 1.7, about 1.65, about 1.6, about 1.55, about 1.5, about 1.45, about 1.4, about 1.35, about 1.3, about 1.25, about 1.2, about 1.15, about 1.1, about 1.05, about 1.0, about 0.95, or about 0.9 (inclusive); about 0.9 to about 2.0, about 1.95, about 1.9, about 1.85, about 1.8, about 1.75, about 1.7, about 1.65, about 1.6, about 1.55, about 1.5, about 1.45, about 1.4, about 1.35, about 1.3, about 1.25, about 1.2, about 1.15, about 1.1, about 1.05, about 1.0, or about 0.95 (inclusive); about 0.95 to about 2.0, about 1.95, about 1.9, about 1.85, about 1.8, about 1.75, about 1.7, about 1.65, about 1.6, about 1.55, about 1.5, about 1.45, about 1.4, about 1.35, about 1.3, about 1.25, about 1.2, about 1.15, about 1.1, about 1.05, or about 1.0 (inclusive); about 1.0 to about 2.0, about 1.95, about 1.9, about 1.85, about 1.8, about 1.75, about 1.7, about 1.65, about 1.6, about 1.55, about 1.5, about 1.45, about 1.4, about 1.35, about 1.3, about 1.25, about 1.2, about 1.15, about 1.1, or about 1.05 (inclusive); about 1.05 to about 2.0, about 1.95, about 1.9, about 1.85, about 1.8, about 1.75, about 1.7, about 1.65, about 1.6, about 1.55, about 1.5, about 1.45, about 1.4, about 1.35, about 1.3, about 1.25, about 1.2, about 1.15, or about 1.1 (inclusive); about 1.1 to about 2.0, about 1.95, about 1.9, about 1.85, about 1.8, about 1.75, about 1.7, about 1.65, about 1.6, about 1.55, about 1.5, about 1.45, about 1.4, about 1.35, about 1.3, about 1.25, about 1.2, or about 1.15 (inclusive); about 1.15 to about 2.0, about 1.95, about 1.9, about 1.85, about 1.8, about 1.75, about 1.7, about 1.65, about 1.6, about 1.55, about 1.5, about 1.45, about 1.4, about 1.35, about 1.3, about 1.25, or about 1.2 (inclusive); about 1.2 to about 2.0, about 1.95, about 1.9, about 1.85, about 1.8, about 1.75, about 1.7, about 1.65, about 1.6, about 1.55, about 1.5, about 1.45, about 1.4, about 1.35, about 1.3, or about 1.25 (inclusive); about 1.25 to about 2.0, about 1.95, about 1.9, about 1.85, about 1.8, about 1.75, about 1.7, about 1.65, about 1.6, about 1.55, about 1.5, about 1.45, about 1.4, about 1.35, or about 1.3 (inclusive); about 1.3 to about 2.0, about 1.95, about 1.9, about 1.85, about 1.8, about 1.75, about 1.7, about 1.65, about 1.6, about 1.55, about 1.5, about 1.45, about 1.4, or about 1.35 (inclusive); about 1.35 to about 2.0, about 1.95, about 1.9, about 1.85, about 1.8, about 1.75, about 1.7, about 1.65, about 1.6, about 1.55, about 1.5, about 1.45, or about 1.4 (inclusive); about 1.4 to about 2.0, about 1.95, about 1.9, about 1.85, about 1.8, about 1.75, about 1.7, about 1.65, about 1.6, about 1.55, about 1.5, or about 1.45 (inclusive); about 1.45 to about 2.0, about 1.95, about 1.9, about 1.85, about 1.8, about 1.75, about 1.7, about 1.65, about 1.6, about 1.55, or about 1.5 (inclusive); about 1.5 to about 2.0, about 1.95, about 1.9, about 1.85, about 1.8, about 1.75, about 1.7, about 1.65, about 1.6, or about 1.55 (inclusive); about 1.55 to about 2.0, about 1.95, about 1.9, about 1.85, about 1.8, about 1.75, about 1.7, about 1.65, or about 1.6 (inclusive); about 1.6 to about 2.0, about 1.95, about 1.9, about 1.85, about 1.8, about 1.75, about 1.7, or about 1.65 (inclusive); about 1.65 to about 2.0, about 1.95, about 1.9, about 1.85, about 1.8, about 1.75, about 1.7, or about 1.7 (inclusive); about 1.7 to about 2.0, about 1.95, about 1.9, about 1.85, about 1.8, or about 1.75 (inclusive); about 1.75 to about 2.0, about 1.95, about 1.9, about 1.85, or about 1.8 (inclusive); about 1.8 to about 2.0, about 1.95, about 1.9, or about 1.85 (inclusive); about 1.85 to about 2.0, about 1.95, or about 1.9 (inclusive); about 1.9 to about 2.0 or about 1.95 (inclusive); or about 1.95 to about 2.0 (inclusive), when using Formula XI, and a UCS that is above the reference value indicates that the urine sample is a natural urine sample. In some embodiments, the reference value can be, e.g., about 0.80, about 0.85, about 0.90, about 0.95, about 1.0, about 1.05, about 1.1, about 1.15, about 1.2, about 1.25, about 1.3, about 1.35, about 1.4, about 1.45, about 1.5, about 1.55, about 1.6, about 1.65, about 1.7, about 1.75, about 1.8, about 1.85, about 1.9, about 1.95, or about 2.0, when using Formula XI, and a UCS that is above the reference value indicates that the urine sample is a natural urine sample.

For Formula XI, if the determined UCS is within a range of reference values, it indicates that the urine sample is a diluted urine sample. As described above, a range of appropriate reference values for identifying a diluted urine sample can be determined by the training dataset (e.g., any of the exemplary training datasets described herein). In some embodiments, a range of reference values for identifying a diluted urine sample can be selected because the range of reference values has the highest accuracy when the range of reference values is applied to a training dataset (e.g., any of the exemplary training datasets described herein). In some embodiments, a range of reference values for identifying a diluted urine sample is selected because the range of reference values has the highest area under the curve (AUC) for receiver operating characteristic (ROC) when the range of reference values is applied to a training dataset (e.g., any of the exemplary training datasets described herein). In some embodiments, the range of reference values (e.g., threshold value) can be, e.g., about 0.25 to about 0.80, about 0.78, about 0.76, about 0.74, about 0.72, about 0.70, about 0.68, about 0.66, about 0.64, about 0.62, about 0.60, about 0.58, about 0.56, about 0.54, about 0.52, about 0.50, about 0.48, about 0.46, about 0.44, about 0.42, about 0.40, about 0.38, about 0.36, about 0.34, about 0.32, about 0.30, about 0.28, or about 0.26 (inclusive); about 0.26 to about 0.80, about 0.78, about 0.76, about 0.74, about 0.72, about 0.70, about 0.68, about 0.66, about 0.64, about 0.62, about 0.60, about 0.58, about 0.56, about 0.54, about 0.52, about 0.50, about 0.48, about 0.46, about 0.44, about 0.42, about 0.40, about 0.38, about 0.36, about 0.34, about 0.32, about 0.30, or about 0.28 (inclusive); about 0.28 to about 0.80, about 0.78, about 0.76, about 0.74, about 0.72, about 0.70, about 0.68, about 0.66, about 0.64, about 0.62, about 0.60, about 0.58, about 0.56, about 0.54, about 0.52, about 0.50, about 0.48, about 0.46, about 0.44, about 0.42, about 0.40, about 0.38, about 0.36, about 0.34, about 0.32, or about 0.30 (inclusive); about 0.30 to about 0.80, about 0.78, about 0.76, about 0.74, about 0.72, about 0.70, about 0.68, about 0.66, about 0.64, about 0.62, about 0.60, about 0.58, about 0.56, about 0.54, about 0.52, about 0.50, about 0.48, about 0.46, about 0.44, about 0.42, about 0.40, about 0.38, about 0.36, about 0.34, or about 0.32 (inclusive); about 0.32 to about 0.80, about 0.78, about 0.76, about 0.74, about 0.72, about 0.70, about 0.68, about 0.66, about 0.64, about 0.62, about 0.60, about 0.58, about 0.56, about 0.54, about 0.52, about 0.50, about 0.48, about 0.46, about 0.44, about 0.42, about 0.40, about 0.38, about 0.36, or about 0.34 (inclusive); about 0.34 to about 0.80, about 0.78, about 0.76, about 0.74, about 0.72, about 0.70, about 0.68, about 0.66, about 0.64, about 0.62, about 0.60, about 0.58, about 0.56, about 0.54, about 0.52, about 0.50, about 0.48, about 0.46, about 0.44, about 0.42, about 0.40, about 0.38, or about 0.36 (inclusive); about 0.36 to about 0.80, about 0.78, about 0.76, about 0.74, about 0.72, about 0.70, about 0.68, about 0.66, about 0.64, about 0.62, about 0.60, about 0.58, about 0.56, about 0.54, about 0.52, about 0.50, about 0.48, about 0.46, about 0.44, about 0.42, about 0.40, or about 0.38 (inclusive); about 0.38 to about 0.80, about 0.78, about 0.76, about 0.74, about 0.72, about 0.70, about 0.68, about 0.66, about 0.64, about 0.62, about 0.60, about 0.58, about 0.56, about 0.54, about 0.52, about 0.50, about 0.48, about 0.46, about 0.44, about 0.42, or about 0.40 (inclusive); about 0.40 to about 0.80, about 0.78, about 0.76, about 0.74, about 0.72, about 0.70, about 0.68, about 0.66, about 0.64, about 0.62, about 0.60, about 0.58, about 0.56, about 0.54, about 0.52, about 0.50, about 0.48, about 0.46, about 0.44, or about 0.42 (inclusive); about 0.42 to about 0.80, about 0.78, about 0.76, about 0.74, about 0.72, about 0.70, about 0.68, about 0.66, about 0.64, about 0.62, about 0.60, about 0.58, about 0.56, about 0.54, about 0.52, about 0.50, about 0.48, about 0.46, or about 0.44 (inclusive); about 0.44 to about 0.80, about 0.78, about 0.76, about 0.74, about 0.72, about 0.70, about 0.68, about 0.66, about 0.64, about 0.62, about 0.60, about 0.58, about 0.56, about 0.54, about 0.52, about 0.50, about 0.48, or about 0.46 (inclusive); about 0.46 to about 0.80, about 0.78, about 0.76, about 0.74, about 0.72, about 0.70, about 0.68, about 0.66, about 0.64, about 0.62, about 0.60, about 0.58, about 0.56, about 0.54, about 0.52, about 0.50, or about 0.48 (inclusive); about 0.48 to about 0.80, about 0.78, about 0.76, about 0.74, about 0.72, about 0.70, about 0.68, about 0.66, about 0.64, about 0.62, about 0.60, about 0.58, about 0.56, about 0.54, about 0.52, or about 0.50 (inclusive); about 0.50 to about 0.80, about 0.78, about 0.76, about 0.74, about 0.72, about 0.70, about 0.68, about 0.66, about 0.64, about 0.62, about 0.60, about 0.58, about 0.56, about 0.54, or about 0.52 (inclusive); about 0.52 to about 0.80, about 0.78, about 0.76, about 0.74, about 0.72, about 0.70, about 0.68, about 0.66, about 0.64, about 0.62, about 0.60, about 0.58, about 0.56, or about 0.54 (inclusive); about 0.54 to about 0.80, about 0.78, about 0.76, about 0.74, about 0.72, about 0.70, about 0.68, about 0.66, about 0.64, about 0.62, about 0.60, about 0.58, or about 0.56 (inclusive); about 0.56 to about 0.80, about 0.78, about 0.76, about 0.74, about 0.72, about 0.70, about 0.68, about 0.66, about 0.64, about 0.62, about 0.60, or about 0.58 (inclusive); about 0.58 to about 0.80, about 0.78, about 0.76, about 0.74, about 0.72, about 0.70, about 0.68, about 0.66, about 0.64, about 0.62, or about 0.60 (inclusive); about 0.60 to about 0.80, about 0.78, about 0.76, about 0.74, about 0.72, about 0.70, about 0.68, about 0.66, about 0.64, or about 0.62 (inclusive); about 0.62 to about 0.80, about 0.78, about 0.76, about 0.74, about 0.72, about 0.70, about 0.68, about 0.66, or about 0.64 (inclusive); about 0.64 to about 0.80, about 0.78, about 0.76, about 0.74, about 0.72, about 0.70, about 0.68, or about 0.66 (inclusive); about 0.66 to about 0.80, about 0.78, about 0.76, about 0.74, about 0.72, about 0.70, or about 0.68 (inclusive); about 0.68 to about 0.80, about 0.78, about 0.76, about 0.74, about 0.72, or about 0.70 (inclusive); about 0.70 to about 0.80, about 0.78, about 0.76, about 0.74, or about 0.72 (inclusive); about 0.72 to about 0.80, about 0.78, about 0.76, or about 0.74 (inclusive); about 0.74 to about 0.80, about 0.78, or about 0.76 (inclusive); about 0.76 to about 0.80 or about 0.78 (inclusive); or about 0.78 to about 0.80 (inclusive), when using Formula XI, and a UCS that is within the range of the reference values indicates that the urine sample is a diluted urine sample.

In some embodiments, the UCS is generated using the following formula:

$$UCS = 10 \times \log(A1/A2). \quad \text{(XII)}$$

For Formula XII, if the determined UCS is below than a reference value (e.g., a threshold value), it indicates that the urine sample is a synthetic urine sample. An appropriate reference value (e.g., threshold value) for identifying a synthetic urine sample can be determined by the training dataset (e.g., any of the exemplary training datasets described herein). In some embodiments, a reference value (e.g., threshold value) for identifying a synthetic urine sample is selected because the reference value has the highest accuracy when the reference value is applied to a training dataset (e.g., any of the exemplary training datasets described herein). In some embodiments, a reference value for identifying a synthetic urine sample is selected because the reference value (e.g., threshold value) has the highest area under the curve (AUC) for receiver operating characteristic (ROC) when the reference value is applied to a training dataset (e.g., any of the exemplary training datasets described herein). In some embodiments, the reference value (e.g., threshold value) can be any value from, e.g., about −20.0 to about −6.0, about −6.5, about −7.0, about −7.5, about −8.0, about −8.5, about −9.0, about −9.5, about −10.0, about −10.5, about −11.0, about −11.5, about −12.0, about −12.5, about −13.0, about −13.5, about −14.0, about −14.5, about −15.0, about −15.5, about −16.0, about −16.5, about −17.0, about −17.5, about −18.0, about −18.5, about −19.0, or about −19.5 (inclusive); about −19.5 to about −6.0, about −6.5, about −7.0, about −7.5, about −8.0, about −8.5, about −9.0, about −9.5, about −10.0, about −10.5, about −11.0, about −11.5, about −12.0, about −12.5, about −13.0, about −13.5, about −14.0, about −14.5, about −15.0, about −15.5, about −16.0, about −16.5, about −17.0, about −17.5, about −18.0, about −18.5, or about −19.0 (inclusive); about −19.0 to about −6.0, about −6.5, about −7.0, about −7.5, about −8.0, about −8.5, about −9.0, about −9.5, about −10.0, about −10.5, about −11.0, about −11.5, about −12.0, about −12.5, about −13.0, about −13.5, about −14.0, about −14.5, about −15.0, about −15.5, about −16.0, about −16.5, about −17.0, about −17.5, about −18.0, or about −18.5 (inclusive); about −18.5 to about −6.0, about −6.5, about −7.0, about −7.5, about −8.0, about −8.5, about −9.0, about −9.5, about −10.0, about −10.5, about −11.0, about −11.5, about −12.0, about −12.5, about −13.0, about −13.5, about −14.0, about −14.5, about −15.0, about −15.5, about −16.0, about −16.5, about −17.0, about −17.5, or about −18.0 (inclusive); about −18.0 to about −6.0, about −6.5, about −7.0, about −7.5, about −8.0, about −8.5, about −9.0, about −9.5, about −10.0, about −10.5, about −11.0, about −11.5, about −12.0, about −12.5, about −13.0, about −13.5, about −14.0, about −14.5, about −15.0, about −15.5, about −16.0, about −16.5, about −17.0, or about −17.5 (inclusive); about −17.5 to about −6.0, about −6.5, about −7.0, about −7.5, about −8.0, about −8.5, about −9.0, about −9.5, about −10.0, about −10.5, about −11.0, about −11.5, about −12.0, about −12.5, about −13.0, about −13.5, about −14.0, about −14.5, about −15.0, about −15.5, about −16.0, about −16.5, or about −17.0 (inclusive); about −17.0 to about −6.0, about −6.5, about −7.0, about −7.5, about −8.0, about −8.5, about −9.0, about −9.5, about −10.0, about −10.5, about −11.0, about −11.5, about −12.0, about −12.5, about −13.0, about −13.5, about −14.0, about −14.5, about −15.0, about −15.5, about −16.0, or about −16.5 (inclusive); about −16.5 to about −6.0, about −6.5, about −7.0, about −7.5, about −8.0, about −8.5, about −9.0, about −9.5, about −10.0, about −10.5, about −11.0, about −11.5, about −12.0, about −12.5, about −13.0, about −13.5, about −14.0, about −14.5, about −15.0, about −15.5, or about −16.0 (inclusive); about −16.0 to about −6.0, about −6.5, about −7.0, about −7.5, about −8.0, about −8.5, about −9.0, about −9.5, about −10.0, about −10.5, about −11.0, about −11.5, about −12.0, about −12.5, about −13.0, about −13.5, about −14.0, about −14.5, about −15.0, or about −15.5 (inclusive); about −15.5 to about −6.0, about −6.5, about −7.0, about −7.5, about −8.0, about −8.5, about −9.0, about −9.5, about −10.0, about −10.5, about −11.0, about −11.5, about −12.0, about −12.5, about −13.0, about −13.5, about −14.0, about −14.5, or about −15.0 (inclusive); about −15.0 to about −6.0, about −6.5, about −7.0, about −7.5, about −8.0, about −8.5, about −9.0, about −9.5, about −10.0, about −10.5, about −11.0, about −11.5, about −12.0, about −12.5, about −13.0, about −13.5, about −14.0, or about −14.5 (inclusive); about −14.5 to about −6.0, about −6.5, about −7.0, about −7.5, about −8.0, about −8.5, about −9.0, about −9.5, about −10.0, about −10.5, about −11.0, about −11.5, about −12.0, about −12.5, about −13.0, about −13.5, or about −14.0 (inclusive); about −14.0 to about −6.0, about −6.5, about −7.0, about −7.5, about −8.0, about −8.5, about −9.0, about −9.5, about −10.0, about −10.5, about −11.0, about −11.5, about −12.0, about −12.5, about −13.0, or about −13.5 (inclusive); about −13.5 to about −6.0, about −6.5, about −7.0, about −7.5, about −8.0, about −8.5, about −9.0, about −9.5, about −10.0, about −10.5, about −11.0, about −11.5, about −12.0, about −12.5, or about −13.0 (inclusive); about −13.0 to about −6.0, about −6.5, about −7.0, about −7.5, about −8.0, about −8.5, about −9.0, about −9.5, about −10.0, about −10.5, about −11.0, about −11.5, about −12.0, or about −12.5 (inclusive); about −12.5 to about −6.0, about −6.5, about −7.0, about −7.5, about −8.0, about −8.5, about −9.0, about −9.5, about −10.0, about −10.5, about −11.0, about −11.5, or about −12.0 (inclusive); about −12.0 to about −6.0, about −6.5, about −7.0, about −7.5, about −8.0, about −8.5, about −9.0, about −9.5, about −10.0, about −10.5, about −11.0, or about −11.5 (inclusive); about −11.5 to about −6.0, about −6.5, about −7.0, about −7.5, about −8.0, about −8.5, about −9.0, about −9.5, about −10.0, about −10.5, or about −11.0 (inclusive); about −11.0 to about −6.0, about −6.5, about −7.0, about −7.5, about −8.0, about −8.5, about −9.0, about −9.5, about −10.0, or about −10.5 (inclusive); about −10.5 to about −6.0, about −6.5, about −7.0, about −7.5, about −8.0, about −8.5, about −9.0, about −9.5, or about −10.0 (inclusive); about −10.0 to about −6.0, about −6.5, about −7.0, about −7.5, about −8.0, about −8.5, about −9.0, or about −9.5 (inclusive); about −9.5 to about −6.0, about −6.5, about −7.0, about −7.5, about −8.0, about −8.5, or about −9.0 (inclusive); about −9.0 to about −6.0, about −6.5, about −7.0, about −7.5, about −8.0, or about −8.5 (inclusive); about −8.5 to about −6.0, about −6.5, about −7.0, about −7.5, or about −8.0 (inclusive); about −8.0 to about −6.0, about −6.5, about −7.0, or about −7.5 (inclusive); about −7.5 to about −6.0, about −6.5, or about −7.0 (inclusive); about −7.0 to about −6.0, or about −6.5 (inclusive); or about −6.5 to about −6.0 (inclusive), when using Formula XII, and a UCS that is below the reference value indicates that the urine sample is a synthetic urine sample. In some embodiments, the reference value can be, e.g., about −6.0, about −6.5, about −7.0, about −7.5, about −8.0, about −8.5, about −9.0, about −9.5, about −10.0, about −10.5, about −11.0, about −11.5, about −12.0, about −12.5, about −13.0, about −13.5, about −14.0, about −14.5, about −15.0, about −15.5, about −16.0, about −16.5, about −17.0, about −17.5, about −18.0, about −18.5, about −19.0, about −19.5, or about −20.0, when using Formula XII, and a UCS that is below the reference value indicates that the urine sample is a synthetic urine sample.

For Formula XII, if the determined UCS is within a range of reference values, it indicates that the urine sample is a diluted urine sample. As described above, a range of appropriate reference values for identifying a diluted urine sample can be determined by the training dataset (e.g., any of the exemplary training datasets described herein). In some embodiments, a range of reference values for identifying a diluted urine sample can be selected because the range of reference values has the highest accuracy when the range of reference values is applied to a training dataset (e.g., any of the exemplary training datasets described herein). In some embodiments, a range of reference values for identifying a diluted urine sample is selected because the range of reference values has the highest area under the curve (AUC) for receiver operating characteristic (ROC) when the range of reference values is applied to a training dataset (e.g., any of the exemplary training datasets described herein). In some embodiments, the range of reference values (e.g., threshold value) can be, e.g., about −6.0 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, about −4.3, about −4.4, about −4.5, about −4.6, about −4.7, about −4.8, about −4.9, about −5.0, about −5.1, about −5.2, about −5.3, about −5.4, about −5.5, about −5.6, about −5.7, about −5.8, or about −5.9 (inclusive); about −5.9 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, about −4.3, about −4.4, about −4.5, about −4.6, about −4.7, about −4.8, about −4.9, about −5.0, about −5.1, about −5.2, about −5.3, about −5.4, about −5.5, about −5.6, about −5.7, or about −5.8 (inclusive); about −5.8 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, about −4.3, about −4.4, about −4.5, about −4.6, about −4.7, about −4.8, about −4.9, about −5.0, about −5.1, about −5.2, about −5.3, about −5.4, about −5.5, about −5.6, or about −5.7 (inclusive); about −5.7 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, about −4.3, about −4.4, about −4.5, about −4.6, about −4.7, about −4.8, about −4.9, about −5.0, about −5.1, about −5.2, about −5.3, about −5.4, about −5.5, or about −5.6 (inclusive); about −5.6 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, about −4.3, about −4.4, about −4.5, about −4.6, about −4.7, about −4.8, about −4.9, about −5.0, about −5.1, about −5.2, about −5.3, about −5.4, or about −5.5 (inclusive); about −5.5 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, about −4.3, about −4.4, about −4.5, about −4.6, about −4.7, about −4.8, about −4.9, about −5.0, about −5.1, about −5.2, about −5.3, or about −5.4 (inclusive); about −5.4 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, about −4.3, about −4.4, about −4.5, about −4.6, about −4.7, about −4.8, about −4.9, about −5.0, about −5.1, about −5.2, or about −5.3 (inclusive); about −5.3 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, about −4.3, about −4.4, about −4.5, about −4.6, about −4.7, about −4.8, about −4.9, about −5.0, about −5.1, or about −5.2 (inclusive); about −5.2 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, about −4.3, about −4.4, about −4.5, about −4.6, about −4.7, about −4.8, about −4.9, about −5.0, or about −5.1 (inclusive); about −5.1 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, about −4.3, about −4.4, about −4.5, about −4.6, about −4.7, about −4.8, about −4.9, or about −5.0 (inclusive); about −5.0 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, about −4.3, about −4.4, about −4.5, about −4.6, about −4.7, about −4.8, or about −4.9 (inclusive); about −4.9 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, about −4.3, about −4.4, about −4.5, about −4.6, about −4.7, or about −4.8 (inclusive); about −4.8 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, about −4.3, about −4.4, about −4.5, about −4.6, or about −4.7 (inclusive); about −4.7 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, about −4.3, about −4.4, about −4.5, or about −4.6 (inclusive); about −4.6 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, about −4.3, about −4.4, or about −4.5 (inclusive); about −4.5 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, about −4.3, or about −4.4 (inclusive); about −4.4 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, about −4.2, or about −4.3 (inclusive); about −4.3 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, about −4.1, or about −4.2 (inclusive); about −4.2 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, about −4.0, or about −4.1 (inclusive); about −4.1 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, about −3.9, or about −4.0 (inclusive); about −4.0 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, about −3.8, or about −3.9 (inclusive); about −3.9 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, about −3.7, or about −3.8 (inclusive); about −3.8 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, about −3.6, or about −3.7 (inclusive); about −3.7 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, about −3.5, or about −3.6 (inclusive); about −3.6 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, about −3.4, or about −3.5 (inclusive); about −3.5 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, about −3.3, or about −3.4 (inclusive); about −3.4 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, about −3.2, or about −3.3 (inclusive); about −3.3 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, about −3.1, or about −3.2 (inclusive); about −3.2 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, about −3.0, or about −3.1 (inclusive); about −3.1 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, about −2.9, or about −3.0 (inclusive); about −3.0 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, about −2.8, or about −2.9 (inclusive); about −2.9 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, about −2.7, or about −2.8 (inclusive); about −2.8 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, about −2.6, or about −2.7 (inclusive); about −2.7 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, about −2.5, or about −2.6 (inclusive); about −2.6 to about −1.0, about −1.1, about −1.2, about −1.3, about −1.4, about −1.5, about −1.6, about −1.7, about −1.8, about −1.9, about −2.0, about −2.1, about −2.2, about −2.3, about −2.4, or about −2.5 (inclusive); about −2.5 to about −1.0, about −1.1, about −1.2, about −1.3, about −1.4, about −1.5, about −1.6, about −1.7, about −1.8, about −1.9, about −2.0, about −2.1, about −2.2, about −2.3, or about −2.4 (inclusive); about −2.4 to about −1.0, about −1.1, about −1.2, about −1.3, about −1.4, about −1.5, about −1.6, about −1.7, about −1.8, about −1.9, about −2.0, about −2.1, about −2.2, or about −2.3 (inclusive); about −2.3 to about −1.0, about −1.1, about −1.2, about −1.3, about −1.4, about −1.5, about −1.6, about −1.7, about −1.8, about −1.9, about −2.0, about −2.1, or about −2.2 (inclusive); about −2.2 to about −1.0, about −1.1, about −1.2, about −1.3, about −1.4, about −1.5, about −1.6, about −1.7, about −1.8, about −1.9, about −2.0, or about −2.1 (inclusive); about −2.1 to about −1.0, about −1.1, about −1.2, about −1.3, about −1.4, about −1.5, about −1.6, about −1.7, about −1.8, about −1.9, or about −2.0 (inclusive); about −2.0 to about −1.0, about −1.1, about −1.2, about −1.3, about −1.4, about −1.5, about −1.6, about −1.7, about −1.8, or about −1.9 (inclusive); about −1.9 to about −1.0, about −1.1, about −1.2, about −1.3, about −1.4, about −1.5, about −1.6, about −1.7, or about −1.8 (inclusive); about −1.8 to about −1.0, about −1.1, about −1.2, about −1.3, about −1.4, about −1.5, about −1.6, or about −1.7 (inclusive); about −1.7 to about −1.0, about −1.1, about −1.2, about −1.3, about −1.4, about −1.5, or about −1.6 (inclusive); about −1.6 to about −1.0, about −1.1, about −1.2, about −1.3, about −1.4, or about −1.5 (inclusive); about −1.5 to about −1.0, about −1.1, about −1.2, about −1.3, or about −1.4 (inclusive); about −1.4 to about −1.0, about −1.1, about −1.2, or about −1.3 (inclusive); about −1.3 to about −1.0, about −1.1, or about −1.2 (inclusive); about −1.2 to about −1.0 or about −1.1 (inclusive); or about −1.1 to about −1.0 (inclusive), when using Formula XII, and a UCS that is within the range of the reference values indicates that the urine sample is a diluted urine sample.

For Formula XII, if the determined UCS is above a reference value (e.g., a threshold value), it indicates that the urine sample is a natural urine sample. As described above, an appropriate reference value (e.g., threshold value) for identifying a natural urine sample can be determined by the training dataset (e.g., any of the exemplary training datasets described herein). In some embodiments, a reference value (e.g., threshold value) for identifying a natural urine sample can be selected because the reference value has the highest accuracy when the reference value is applied to a training dataset (e.g., any of the exemplary training datasets described herein). In some embodiments, a reference value for identifying a natural urine sample is selected because the reference value (e.g., threshold value) has the highest area under the curve (AUC) for receiver operating characteristic (ROC) when the reference value is applied to a training dataset (e.g., any of the exemplary training datasets described herein). In some embodiments, the reference value (e.g., threshold value) can be any value from, e.g., about −1.0 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, about 0.3, about 0.2, about 0.1, about 0, about −0.1, about −0.2, about −0.3, about −0.4, about −0.5, about −0.6, about −0.7, about −0.8, or about −0.9 (inclusive); about −0.9 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, about 0.3, about 0.2, about 0.1, about 0, about −0.1, about −0.2, about −0.3, about −0.4, about −0.5, about −0.6, about −0.7, or about −0.8 (inclusive); about −0.8 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, about 0.3, about 0.2, about 0.1, about 0, about −0.1, about −0.2, about −0.3, about −0.4, about −0.5, about −0.6, or about −0.7 (inclusive); about −0.7 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, about 0.3, about 0.2, about 0.1, about 0, about −0.1, about −0.2, about −0.3, about −0.4, about −0.5, or about −0.6 (inclusive); about −0.6 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, about 0.3, about 0.2, about 0.1, about 0, about −0.1, about −0.2, about −0.3, about −0.4, or about −0.5 (inclusive); about −0.5 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, about 0.3, about 0.2, about 0.1, about 0, about −0.1, about −0.2, about −0.3, or about −0.4 (inclusive); about −0.4 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, about 0.3, about 0.2, about 0.1, about 0, about −0.1, about −0.2, or about −0.3 (inclusive); about −0.3 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, about 0.3, about 0.2, about 0.1, about 0, about −0.1, or about −0.2 (inclusive); about −0.2 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, about 0.3, about 0.2, about 0.1, about 0, or about −0.1 (inclusive); about −0.1 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, about 0.3, about 0.2, about 0.1, or about 0 (inclusive); about 0 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, about 0.3, about 0.2, or about 0.1 (inclusive); about 0.1 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, about 0.3, or about 0.2 (inclusive); about 0.2 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, or about 0.3 (inclusive); about 0.3 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, or about 0.4 (inclusive); about 0.4 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, or about 0.5 (inclusive); about 0.5 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, or about 0.6 (inclusive); about 0.6 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, or about 0.7 (inclusive); about 0.7 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, or about 0.8 (inclusive); about 0.8 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, or about 0.9 (inclusive); about 0.9 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, or about 1.0 (inclusive); about 1.0 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, or about 1.1 (inclusive); about 1.1 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, or about 1.2 (inclusive); about 1.2 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, or about 1.3 (inclusive); about 1.3 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, or about 1.4 (inclusive); about 1.4 to about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, or about 1.5 (inclusive); about 1.5 to about 3.0, about 2.9, about 2.8, about 2.7, about 2.6, about 2.5, about 2.4, about 2.3, about 2.2, about 2.1, about 2.0, about 1.9, about 1.8, about 1.7, or about 1.6 (inclusive); about 1.6 to about 3.0, about 2.9, about 2.8, about 2.7, about 2.6, about 2.5, about 2.4, about 2.3, about 2.2, about 2.1, about 2.0, about 1.9, about 1.8, or about 1.7 (inclusive); about 1.7 to about 3.0, about 2.9, about 2.8, about 2.7, about 2.6, about 2.5, about 2.4, about 2.3, about 2.2, about 2.1, about 2.0, about 1.9, or about 1.8 (inclusive); about 1.8 to about 3.0, about 2.9, about 2.8, about 2.7, about 2.6, about 2.5, about 2.4, about 2.3, about 2.2, about 2.1, about 2.0, or about 1.9 (inclusive); about 1.9 to about 3.0, about 2.9, about 2.8, about 2.7, about 2.6, about 2.5, about 2.4, about 2.3, about 2.2, about 2.1, or about 2.0 (inclusive); about 2.0 to about 3.0, about 2.9, about 2.8, about 2.7, about 2.6, about 2.5, about 2.4, about 2.3, about 2.2, or about 2.1 (inclusive); about 2.1 to about 3.0, about 2.9, about 2.8, about 2.7, about 2.6, about 2.5, about 2.4, about 2.3, or about 2.2 (inclusive); about 2.2 to about 3.0, about 2.9, about 2.8, about 2.7, about 2.6, about 2.5, about 2.4, or about 2.3 (inclusive); about 2.3 to about 3.0, about 2.9, about 2.8, about 2.7, about 2.6, about 2.5, or about 2.4 (inclusive); about 2.4 to about 3.0, about 2.9, about 2.8, about 2.7, about 2.6, or about 2.5 (inclusive); about 2.5 to about 3.0, about 2.9, about 2.8, about 2.7, or about 2.6 (inclusive); about 2.6 to about 3.0, about 2.9, about 2.8, or about 2.7 (inclusive); about 2.7 to about 3.0, about 2.9, or about 2.8 (inclusive); about 2.8 to about 3.0 or about 2.9 (inclusive); or about 2.9 to about 3.0 (inclusive), when using Formula XI, and a UCS that is above the reference value indicates that the urine sample is a natural urine sample. In some embodiments, the reference value can be, e.g., about −1.0, about −0.9, about −0.8, about −0.7, about −0.6, about −0.5, about −0.4, about −0.3, about −0.2, about −0.1, about 0, about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0, when using Formula XI, and a UCS that is above the reference value indicates that the urine sample is a natural urine sample.

Some examples of the methods described herein further include a step of comparing the determined absorbance at 280 nm of a urine sample to a reference 280 nm absorbance value, where a decreased in the determined absorbance at 280 nm as compared to the reference 280 nm absorbance value indicates that the urine sample is a diluted urine sample. A reference 280 nm absorbance value can be, e.g., the absorbance at 280 nm of a control natural urine sample (e.g., a natural urine sample obtained from a human subject not receiving one or more illegal or controlled substances). An average level of absorbance at 280 nm in control natural urine samples can be obtained from a subject population (e.g., a subject population not receiving one or more illegal or controlled substances). A reference 280 nm absorbance value can be, e.g., an OD280 of about 0.10, about 0.15, about 0.20, about 0.25, about 0.30, about 0.35, about 0.40, about 0.45, about 0.50, about 0.55, about 0.60, about 0.65, about 0.70, about 0.75, about 0.80, about 0.85, about 0.90, about 0.95, about 1.00, about 1.05, about 1.10, about 1.15, about 1.20, about 1.25, about 1.30, about 1.35, about 1.40, about 1.45, about 1.50, about 1.55, about 1.60, about 1.65, about 1.70, about 1.75, about 1.80, about 1.85, about 1.90, about 1.95, or about 2.00. A reference 280 nm absorbance value can be, e.g., about 0.10 to about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, about 0.3, or about 0.2 (inclusive); about 0.2 to about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, or about 0.3 (inclusive); about 0.3 to about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, or about 0.4 (inclusive); about 0.4 to about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, or about 0.5 (inclusive); about 0.5 to about 2.0, about 1.9, about 1.8, about 1.7, about 1.6, about 1.5, about 1.4, about 1.3, about 1.2, about 1.1, about 1.0, about 0.9, about 0.8, about 0.7, or about 0.6 (inclusive); about 0.6 to about 2.0, about 1.9, about 1.8, about 1.7, about 1.6, about 1.5, about 1.4, about 1.3, about 1.2, about 1.1, about 1.0, about 0.9, about 0.8, or about 0.7 (inclusive); about 0.7 to about 2.0, about 1.9, about 1.8, about 1.7, about 1.6, about 1.5, about 1.4, about 1.3, about 1.2, about 1.1, about 1.0, about 0.9, or about 0.8 (inclusive); about 0.8 to about 2.0, about 1.9, about 1.8, about 1.7, about 1.6, about 1.5, about 1.4, about 1.3, about 1.2, about 1.1, about 1.0, or about 0.9 (inclusive); about 0.9 to about 2.0, about 1.9, about 1.8, about 1.7, about 1.6, about 1.5, about 1.4, about 1.3, about 1.2, about 1.1, or about 1.0 (inclusive); about 1.0 to about 2.0, about 1.9, about 1.8, about 1.7, about 1.6, about 1.5, about 1.4, about 1.3, about 1.2, or about 1.1 (inclusive); about 1.1 to about 2.0, about 1.9, about 1.8, about 1.7, about 1.6, about 1.5, about 1.4, about 1.3, or about 1.2 (inclusive); about 1.2 to about 2.0, about 1.9, about 1.8, about 1.7, about 1.6, about 1.5, about 1.4, or about 1.3 (inclusive); about 1.3 to about 2.0, about 1.9, about 1.8, about 1.7, about 1.6, about 1.5, or about 1.4 (inclusive); about 1.4 to about 2.0, about 1.9, about 1.8, about 1.7, about 1.6, or about 1.5 (inclusive); about 1.5 to about 2.0, about 1.9, about 1.8, about 1.7, or about 1.6 (inclusive); about 1.6 to about 2.0, about 1.9, about 1.8, or about 1.7 (inclusive); about 1.7 to about 2.0, about 1.9, or about 1.8 (inclusive); about 1.8 to about 2.0 or about 1.9 (inclusive); or about 1.9 to about 2.0 (inclusive).

Some examples of the methods described herein further include a step of comparing the determined absorbance at 240 nm of a urine sample to a reference 240 nm absorbance value, where a decreased in the determined absorbance at 240 nm as compared to the reference 240 nm absorbance value indicates that the urine sample is a diluted urine sample. A reference 240 nm absorbance value can be, e.g., the absorbance at 240 nm of a control natural urine sample (e.g., a natural urine sample obtained from a human subject not receiving one or more illegal or controlled substances). An average level of absorbance at 240 nm in control natural urine samples can be obtained from a subject population (e.g., a subject population not receiving one or more illegal or controlled substances). A reference 240 nm absorbance value can be, e.g., an OD240 of about 4.0, about 3.9, about 3.8, about 3.7, about 3.6, about 3.5, about 3.4, about 3.3, about 3.2, about 3.1, about 3.0, about 2.9, about 2.8, about 2.7, about 2.6, about 2.5, about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, about 0.9, about 0.8, about 0.7, about 0.6, about 0.5, about 0.4, about 0.3, or about 0.2. A reference 240 nm absorbance value can be, e.g., about 0.2 to about 4.0, about 3.8, about 3.6, about 3.4, about 3.2, about 3.0, about 2.8, about 2.6, about 2.4, about 2.2, about 2.0, about 1.8, about 1.6, about 1.4, about 1.2, about 1.0, about 0.8, about 0.6, or about 0.4 (inclusive); about 0.4 to about 4.0, about 3.8, about 3.6, about 3.4, about 3.2, about 3.0, about 2.8, about 2.6, about 2.4, about 2.2, about 2.0, about 1.8, about 1.6, about 1.4, about 1.2, about 1.0, about 0.8, or about 0.6 (inclusive); about 0.6 to about 4.0, about 3.8, about 3.6, about 3.4, about 3.2, about 3.0, about 2.8, about 2.6, about 2.4, about 2.2, about 2.0, about 1.8, about 1.6, about 1.4, about 1.2, about 1.0, or about 0.8 (inclusive); about 0.8 to about 4.0, about 3.8, about 3.6, about 3.4, about 3.2, about 3.0, about 2.8, about 2.6, about 2.4, about 2.2, about 2.0, about 1.8, about 1.6, about 1.4, about 1.2, or about 1.0 (inclusive); about 1.0 to about 4.0, about 3.8, about 3.6, about 3.4, about 3.2, about 3.0, about 2.8, about 2.6, about 2.4, about 2.2, about 2.0, about 1.8, about 1.6, about 1.4, or about 1.2 (inclusive); about 1.2 to about 4.0, about 3.8, about 3.6, about 3.4, about 3.2, about 3.0, about 2.8, about 2.6, about 2.4, about 2.2, about 2.0, about 1.8, about 1.6, or about 1.4 (inclusive); about 1.4 to about 4.0, about 3.8, about 3.6, about 3.4, about 3.2, about 3.0, about 2.8, about 2.6, about 2.4, about 2.2, about 2.0, about 1.8, or about 1.6 (inclusive); about 1.6 to about 4.0, about 3.8, about 3.6, about 3.4, about 3.2, about 3.0, about 2.8, about 2.6, about 2.4, about 2.2, about 2.0, or about 1.8 (inclusive); about 1.8 to about 4.0, about 3.8, about 3.6, about 3.4, about 3.2, about 3.0, about 2.8, about 2.6, about 2.4, about 2.2, or about 2.0 (inclusive); about 2.0 to about 4.0, about 3.8, about 3.6, about 3.4, about 3.2, about 3.0, about 2.8, about 2.6, about 2.4, or about 2.2 (inclusive); about 2.2 to about 4.0, about 3.8, about 3.6, about 3.4, about 3.2, about 3.0, about 2.8, about 2.6, or about 2.4 (inclusive); about 2.4 to about 4.0, about 3.8, about 3.6, about 3.4, about 3.2, about 3.0, about 2.8, or about 2.6 (inclusive); about 2.6 to about 4.0, about 3.8, about 3.6, about 3.4, about 3.2, about 3.0, or about 2.8 (inclusive); about 2.8 to about 4.0, about 3.8, about 3.6, about 3.4, about 3.2, or about 3.0 (inclusive); about 3.0 to about 4.0, about 3.8, about 3.6, about 3.4, or about 3.2 (inclusive); about 3.2 to about 4.0, about 3.8, about 3.6, or about 3.4 (inclusive); about 3.4 to about 4.0, about 3.8, or about 3.6 (inclusive); about 3.6 to about 4.0 or about 3.8 (inclusive); or about 3.8 to about 4.0 (inclusive).

In some instances, a urine sample from a subject can be diluted prior to performing the method. In such methods, a reference value to be used in the methods can be generated from control urine samples (e.g., natural urine samples and synthetic urine samples), where the control urine samples are diluted to the same extent using the same diluent.

In some examples of any of these methods, the determining of the absorbance at the A1 and the absorbance at the A2 of the urine sample is performed using high-throughput processing.

The subject in these methods can be any of the subjects described herein. The urine sample can be any of the urine samples or have any of the properties of urine samples described herein. Additional exemplary aspects of these methods are described herein.

Methods of Characterizing a Urine Sample from a Subject that Include Determining a UCI Provided herein are methods of characterizing a urine sample from a subject. In some embodiments, the methods include (a) providing a urine sample from a subject; (b) determining one or more of the light absorption, luminescence, phosphorescence, fluorescence, and chemiluminescence of the urine sample at two or more wavelengths of light; (c) applying one or more eigenvectors derived from a principle component algorithm to a standardized dataset derived from the determined light absorption, luminescence, phosphorescence, fluorescence, and chemiluminescence of the urine sample to generate a Urine Characterization Index (UCI) including one or more values for corresponding principle component(s); and (d) characterizing a urine sample as a natural urine sample, a lyophilized urine sample, a diluted natural urine sample, a synthetic urine sample, or a chemically-adulterated urine sample based on the UCI. In some embodiments, the methods include: (a) providing a urine sample collected from a subject; (b) determining the absorbance at a first wavelength (A1) and the absorbance at a second wavelength (A2) of the urine sample, where the A1 is from about 230 nm to about 250 nm (inclusive), and the A2 is from about 260 nm to about 230 nm (inclusive); (c) applying an algorithm to the determined A1 and the determined A2 to generate a Urine Characterization Score (UCS), where the algorithm includes a ratio of the determined A1 to the determined A2; and (d) characterizing a urine sample as a natural urine sample, an adulterated urine sample, a lyophilized urine sample, a diluted natural urine sample, or a synthetic urine sample based on the UCS.

In some embodiments of these methods, the light absorption of the urine sample at two or more (e.g., three, four, five, six, or seven) wavelengths of light is determined (e.g., any of the exemplary wavelengths of light described herein). In some embodiments of these methods, the light absorption of one or more (e.g., two, three, or four) of ultraviolet light wavelength(s), visible light wavelength(s), near-infrared light wavelength(s), and infrared light wavelength(s) is determined. In some embodiments of these methods, the light absorption of the urine sample is determined at one or more wavelength(s) of about 200 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, about 320 nm, about 300 nm, about 295 nm, about 290 nm, about 285 nm, about 280 nm, about 275 nm, about 270 nm, about 265 nm, about 260 nm, about 255 nm, about 250 nm, about 245 nm, about 240 nm, about 235 nm, about 230 nm, or about 225 nm (inclusive); about 225 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, about 320 nm, about 300 nm, about 295 nm, about 290 nm, about 285 nm, about 280 nm, about 275 nm, about 270 nm, about 265 nm, about 260 nm, about 255 nm, about 250 nm, about 245 nm, about 240 nm, about 235 nm, or about 230 nm (inclusive); about 230 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, about 320 nm, about 300 nm, about 295 nm, about 290 nm, about 285 nm, about 280 nm, about 275 nm, about 270 nm, about 265 nm, about 260 nm, about 255 nm, about 250 nm, about 245 nm, about 240 nm, or about 235 nm (inclusive); about 235 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, about 320 nm, about 300 nm, about 295 nm, about 290 nm, about 285 nm, about 280 nm, about 275 nm, about 270 nm, about 265 nm, about 260 nm, about 255 nm, about 250 nm, about 245 nm, or about 240 nm (inclusive); about 240 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, about 320 nm, about 300 nm, about 295 nm, about 290 nm, about 285 nm, about 280 nm, about 275 nm, about 270 nm, about 265 nm, about 260 nm, about 255 nm, about 250 nm, or about 245 nm (inclusive); about 245 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, about 320 nm, about 300 nm, about 295 nm, about 290 nm, about 285 nm, about 280 nm, about 275 nm, about 270 nm, about 265 nm, about 260 nm, about 255 nm, or about 250 nm (inclusive); about 250 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, about 320 nm, about 300 nm, about 295 nm, about 290 nm, about 285 nm, about 280 nm, about 275 nm, about 270 nm, about 265 nm, about 260 nm, or about 255 nm (inclusive); about 255 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, about 320 nm, about 300 nm, about 295 nm, about 290 nm, about 285 nm, about 280 nm, about 275 nm, about 270 nm, about 265 nm, or about 260 nm (inclusive); about 260 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, about 320 nm, about 300 nm, about 295 nm, about 290 nm, about 285 nm, about 280 nm, about 275 nm, about 270 nm, or about 265 nm (inclusive); about 265 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, about 320 nm, about 300 nm, about 295 nm, about 290 nm, about 285 nm, about 280 nm, about 275 nm, or about 270 nm (inclusive); about 270 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, about 320 nm, about 300 nm, about 295 nm, about 290 nm, about 285 nm, about 280 nm, or about 275 nm (inclusive); about 275 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, about 320 nm, about 300 nm, about 295 nm, about 290 nm, about 285 nm, or about 280 nm (inclusive); about 280 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, about 320 nm, about 300 nm, about 295 nm, about 290 nm, or about 285 nm (inclusive); about 285 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, about 320 nm, about 300 nm, about 295 nm, or about 290 nm (inclusive); about 290 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, about 320 nm, about 300 nm, or about 295 nm (inclusive); about 295 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, about 320 nm, or about 300 nm (inclusive); about 300 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, about 340 nm, or about 320 nm (inclusive); about 320 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, about 360 nm, or about 340 nm (inclusive); about 340 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, about 380 nm, or about 360 nm (inclusive); about 360 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, about 400 nm, or about 380 nm (inclusive); about 380 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, about 420 nm, or about 400 nm (inclusive); about 400 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, about 440 nm, or about 420 nm (inclusive); about 420 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, about 460 nm, or about 440 nm (inclusive); about 440 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, about 480 nm, or about 460 nm (inclusive); about 460 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, or about 480 nm (inclusive); about 480 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, about 520 nm, about 500 nm, or about 500 nm (inclusive); about 500 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, about 540 nm, or about 520 nm (inclusive); about 520 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, about 560 nm, or about 540 nm (inclusive); about 540 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, about 580 nm, or about 560 nm (inclusive); about 560 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, about 600 nm, or about 580 nm (inclusive); about 580 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, about 620 nm, or about 600 nm (inclusive); about 600 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, about 640 nm, or about 620 nm (inclusive); about 620 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, about 660 nm, or about 640 nm (inclusive); about 640 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, about 680 nm, or about 660 nm (inclusive); about 660 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, about 700 nm, or about 680 nm (inclusive); about 680 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, about 720 nm, or about 700 nm (inclusive); about 700 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, about 740 nm, or about 720 nm (inclusive); about 720 nm to about 1000 nm, about 980 nm, about 960 nm, about 940 nm, about 920 nm, about 900 nm, about 880 nm, about 860 nm, about 840 nm, about 820 nm, about 800 nm, about 780 nm, about 760 nm, or about 740 nm (inclusive); about 740 nm to about 1000 nm, about 980 nm, about 960 nm, about 940 nm, about 920 nm, about 900 nm, about 880 nm, about 860 nm, about 840 nm, about 820 nm, about 800 nm, about 780 nm, or about 760 nm (inclusive); about 760 nm to about 1000 nm, about 980 nm, about 960 nm, about 940 nm, about 920 nm, about 900 nm, about 880 nm, about 860 nm, about 840 nm, about 820 nm, about 800 nm, or about 780 nm (inclusive); about 780 nm to about 1000 nm, about 980 nm, about 960 nm, about 940 nm, about 920 nm, about 900 nm, about 880 nm, about 860 nm, about 840 nm, about 820 nm, or about 800 nm (inclusive); about 800 nm to about 1000 nm, about 980 nm, about 960 nm, about 940 nm, about 920 nm, about 900 nm, about 880 nm, about 860 nm, about 840 nm, or about 820 nm (inclusive); about 820 nm to about 1000 nm, about 980 nm, about 960 nm, about 940 nm, about 920 nm, about 900 nm, about 880 nm, about 860 nm, or about 840 nm (inclusive); about 840 nm to about 1000 nm, about 980 nm, about 960 nm, about 940 nm, about 920 nm, about 900 nm, about 880 nm, or about 860 nm (inclusive); about 860 nm to about 1000 nm, about 980 nm, about 960 nm, about 940 nm, about 920 nm, about 900 nm, or about 880 nm (inclusive); about 880 nm to about 1000 nm, about 980 nm, about 960 nm, about 940 nm, about 920 nm, or about 900 nm (inclusive); about 900 nm to about 1000 nm, about 980 nm, about 960 nm, about 940 nm, or about 920 nm (inclusive); about 920 nm to about 1000 nm, about 980 nm, about 960 nm, or about 940 nm (inclusive); about 940 nm to about 1000 nm, about 980 nm, or about 960 nm (inclusive); about 960 nm to about 1000 nm or about 980 nm (inclusive); or about 980 nm to about 1000 nm (inclusive). In some embodiments of these methods, the light absorption of the urine sample is determined at one or more wavelength(s) of about 100 nm to about 180 nm (inclusive), about 100 nm to about 400 nm (inclusive), about 400 nm to about 700 nm (inclusive), about 700 nm to about 2500 nm (inclusive), and/or about 2500 nm to about 10,000 nm (inclusive). In some embodiments of these methods, the light absorption of the urine sample is determined at one or more wavelength(s) selected from the group of: about 100 nm to about 180 nm (inclusive), about 180 nm to about 400 nm (inclusive), about 400 nm to about 700 nm (inclusive), about 700 nm to about 2500 nm (inclusive), and about 2500 nm to 10000 nm (inclusive), or any combination thereof.

Some embodiments of these methods include determining one or more of the luminescence, phosphorescence, fluorescence, chemiluminescence, or bioluminescence of the urine sample. In some embodiments, the one or more of the luminescence, phosphorescence, fluorescence, chemiluminescence, or bioluminecence of the urine sample is detected at any of the wavelengths or wavelength regions described herein.

Some embodiments of these methods can include, e.g., determining the emission phenomena of the urine sample (e.g., heat or black-body radiation). In some embodiments, the emission phenomena of the urine sample is detected at any of the wavelengths or wavelength regions described herein. Some embodiments of these methods include, e.g., determining attenuated total reflectance and/or total internal reflectance of the urine sample.

In some embodiments of any of the methods, one or more of the light absorption, luminescence, phosphorescence, fluorescence, and chemiluminescence of the urine sample arises following the application of electromagnetic energy to the urine sample and/or the introduction of an agent (e.g., a chemical, a substrate, an enzyme, or an antibody) to the urine sample.

Some embodiments of any of the methods described herein can include a step of applying a single eigenvector derived from a principle component algorithm to a standardized dataset derived from the determined light absorption, luminescence, phosphorescence, fluorescence, and/or chemiluminescence of the urine sample to generate a Urine Characterization Index (UCI) including a value corresponding to one principle component. Some embodiments of any of the methods described herein can include a step of applying a single eigenvector derived from a principle component algorithm to a standardized dataset derived from the determined light absorption of the urine sample to generate a Urine Characterization Index (UCI) including a value corresponding to one principle component.

Some embodiments of any of the methods described herein can include a step of applying two eigenvectors derived from a principle component algorithm to a standardized dataset derived from the determined light absorption, luminescence, phosphorescence, fluorescence, and/or chemiluminescence of the urine sample to generate values in two-dimensional principal component space. Some embodiments of any of the methods described herein can include a step of applying two eigenvectors derived from a principle component algorithm to a standardized dataset derived from the determined light absorption of the urine sample to generate values in two-dimensional principal component space.

Some embodiments of any of the methods described herein can include a step of applying three eigenvectors derived from a principle component algorithm to a standardized dataset derived from the determined light absorption, luminescence, phosphorescence, fluorescence, and/or chemiluminescence of the urine sample to generate values in three-dimensional principal component space. Some embodiments of any of the methods described herein can include a step of applying three eigenvectors derived from a principle component algorithm to a standardized dataset derived from the determined light absorption of the urine sample to generate values in three-dimensional principal component space.

Some embodiments of any of the methods described herein can include a step of applying four eigenvectors derived from a principle component algorithm to a standardized dataset derived from the determined light absorption, luminescence, phosphorescence, fluorescence, and/or chemiluminescence of the urine sample to generate values in four-dimensional principal component space. Some embodiments of any of the methods described herein can include a step of applying four eigenvectors derived from a principle component algorithm to a standardized dataset derived from the determined light absorption of the urine sample to generate values in four-dimensional principal component space.

Some embodiments of any of these methods can further include characterizing a urine sample through the use of a clustering algorithm (e.g., a hierarchical clustering algorithm, a k-means clustering algorithm, or a statistical distribution model). Non-limiting examples of clustering algorithms are described herein. Additional examples of clustering algorithms are known in the art.

Some embodiments of any of these methods can further include further characterizing a urine sample by performing regression analysis on the values of the one or more principle component(s). Some embodiments of these methods can further include comparing the determined UCI of the urine sample to a reference UCI of a natural urine sample, a chemically-adulterated urine sample, a lyophilized urine sample, a diluted natural urine sample, or a synthetic urine sample. For example, a urine sample that has a determined UCI that falls within a specific range of reference UCIs of natural urine samples can be identified as a natural urine sample; a urine sample that has a determined UCI that falls within a specific range of reference UCIs of chemically-adulterated urine samples as a chemically-adulterated urine sample; a urine sample that has a determined UCI that falls within a specific range of reference UCIs of lyophilized urine samples as a lyophilized urine sample; a urine sample that has a determined UCI that falls within a specific range of reference UCIs of diluted natural urine samples as a diluted natural urine sample; or a urine sample that has a determined UCI that falls within a specific range of reference UCIs of synthetic urine samples as a synthetic urine sample. The reference UCIs for natural urine samples, chemically-adulterated urine samples, lyophilized urine samples, diluted natural urine samples, and synthetic urine samples can be determined using a training dataset (e.g., any of the exemplary training datasets described herein).

The subject in these methods can be any of the subjects described herein. The urine sample can be any of the urine samples or have any of the properties of urine samples described herein. Additional exemplary aspects of these methods are described herein.

Spectrophotometers

The methods described herein include determining one or more of the light absorption, luminescence, phosphorescence, fluorescence, and chemiluminescence of the urine sample at two or more wavelengths of light. The light absorption, luminescence, phosphorescence, fluorescence, and chemiluminescence of a urine sample can be determined using various spectrophotometers known in the art. Spectrophotometers that can be used in any of the methods described herein are commercially available from a number of vendors, e.g., Beckman Coulter, Inc., Agilent Technologies, Bibby Scientific Ltd., BioTek Instruments, Buck Scientific, Cecil Instruments Ltd., Eppendorf North America, JASCO, Ocean Optics, Shimadzu, Terra Universal Inc., Thermo Scientific, and Biochrom. A high throughput UV-Vis spectrophotometer (e.g., UH4150 UV-Visible-NIR Spectrophotometer from Hitachi High-Tech) can also be used in any of the methods described herein.

In some embodiments, a spectrophotometer can measure the light absorption of a urine sample at a wavelength from, e.g., about 200 nm to about 2500 nm (inclusive), about 200 nm to about 1000 nm (inclusive), about 200 nm to about 340 nm (inclusive), about 230 nm to 250 nm (inclusive), about 260 nm to 340 nm (inclusive), about 200 nm to about 300 nm (inclusive), about 300 nm to about 400 nm (inclusive), about 400 nm to about 500 nm (inclusive), about 500 nm to about 600 nm (inclusive), about 600 nm to about 700 nm (inclusive), about 700 nm to about 800 nm (inclusive), about 800 nm to about 900 nm (inclusive), and/or about 900 nm to about 1000 nm (inclusive).

Some examples of any of the methods described herein further include a step of experimentally diluting a urine sample from the subject (e.g., 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 30-fold, 35-fold, 40-fold, 45-fold, 50-fold, 60-fold, or 64-fold dilution) prior to determination of the absorbance. As is known in the art, a urine sample that has an absorbance at 280 nm (or optionally an absorbance at 240 nm) that exceeds an optical density of greater than 1.0, greater than 1.5, or greater than 2.0 may be diluted (e.g., in water) in order to increase the sensitivity of the measurement of the absorbance by a spectrophotometer. In some embodiments, the concentration of a urine sample can be determined by ratiometric fluorescence indication.

Some embodiments of any of the methods described herein, further include a step of centrifuging a urine sample (or an aliquot of a urine sample or an experimentally diluted natural urine sample) prior to determining the absorbance in order to remove any particulate matter (e.g., mammalian cells, bacteria, nucleic acid, insoluble protein aggregates, soluble protein aggregates, and/or precipitated lipids). Methods for centrifuging a sample (e.g., a urine sample) to remove particulate material are well-known in the art.

Training Dataset and Test Samples

The methods described herein further include creating a dataset for training samples (control urine samples, e.g., control natural urine samples, control diluted natural urine samples, control lyophilized urine samples, control chemically-adulterated urine samples, and/or control synthetic urine samples) and one or more test samples (urine samples from a subject). In some embodiments, a dataset includes multiple data records, wherein each data record includes one or more of the light absorption, luminescence, phosphorescence, fluorescence, and chemiluminescence of a urine sample at two or more wavelengths of light (e.g., as determined using a spectrophotometer).

In some embodiments, the dataset can include data derived from one or more of the determined light absorption, luminescence, phosphorescence, fluorescence, and chemiluminescence of a urine sample at two or more wavelengths of light, e.g., the first derivative of the spectra, the second derivative of the spectra, the statistical moment, standardized moment, or standardized cumulant of a spectral feature including the mean, variance, skewness, kurtosis otherwise known as the 1st, 2nd, 3rd, and 4th statistical moments, slope of the line tangent to any portion of the spectra, or results of the subtraction or addition of two or more spectra. In some embodiments, the dataset can include data indicating the area of one or more of the determined light absorption, luminescence, phosphorescence, fluorescence, and chemiluminescence of a urine sample at two or more wavelengths of light.

In some embodiments, a dataset includes one or more of the light absorption, luminescence, phosphorescence, fluorescence, and chemiluminescence of a urine sample within a certain range of wavelengths, for example, from about 200 nm to 340 nm (inclusive) (e.g., including spectroscopic information at 200 nm, 210 nm, 220 nm, 230 nm, 240 nm, 250 nm, 260 nm, 270 nm, 280 nm, 290 nm, 300 nm, 310 nm, 320 nm, 330 nm, and 340 nm). In some embodiments, a dataset can include spectroscopic information that is collected at every 1 nm, every 5 nm, every 10 nm, every 20 nm, every 50 nm, and every 100 nm wavelengths within a pre-determined wavelength region.

The methods described herein further include forming a training dataset. In some embodiments, samples for forming a training dataset include a plurality of natural urine samples, a plurality of synthetic urine samples, a plurality of chemically-adulterated urine samples, a plurality of lyophilized urine samples, and/or a plurality of diluted natural urine samples. In some embodiments, the number of urine samples for a particular type of urine samples should be chosen so as to achieve a statistically meaningful result. In some embodiments, the training datasets include about 10 to about 20 (inclusive) urine samples of each type of urine sample, about 10 to about 50 (inclusive) urine samples of each type of urine sample, about 50 to about 100 urine samples (inclusive) of each type of urine sample, about 100 to about 500 (inclusive) or each type of urine sample, about 500 to about 1000 urine samples (inclusive) of each type of urine sample, or more than 1000 urine samples of each type of urine sample. In some embodiments, the training datasets include a total of greater than 50 urine samples, greater than 100 urine samples, greater than 150 urine samples, greater than 200 urine samples, greater than 250 urine samples, greater than 300 urine samples, greater than 350 urine samples, greater than 400 urine samples, greater than 450 urine samples, greater than 500 urine samples, greater than 600 urine samples, greater than 700 urine samples, greater than 800 urine samples, greater than 900 urine samples, or greater than 1000 urine samples.

A test sample is a urine sample from a subject whose characteristics need to be determined. The present disclosure provides methods of determining whether a test urine sample (a urine sample obtained from a subject) is a natural urine sample, a synthetic urine sample, a chemically-adulterated urine sample (e.g., a surfactant-adulterated urine sample, a lyophilized urine sample, or a diluted natural urine sample.

In some embodiments, one or more of the determined light absorption, luminescence, phosphorescence, fluorescence, and chemiluminescence at two or more wavelengths of light for a test sample (a urine sample obtained from a subject) and training samples are collected at the same time, and the same experimental procedure is used. In some embodiments, one or more of the determined light absorption, luminescence, phosphorescence, fluorescence, and chemiluminescence at two or more wavelengths of light for the training samples is collected first and a training dataset can be created prior to determining one or more of the determined light absorption, luminescence, phosphorescence, fluorescence, and chemiluminescence at two or more wavelengths of light of a test sample (a urine sample from a subject).

Principal Component Analysis

Principal component analysis (PCA) is a statistical method that uses an orthogonal transformation to convert a set of observations of possibly correlated variables into a set of values of linearly uncorrelated variables called principal components. It finds the principal components of the dataset and transforms the data into a new, lower-dimensional subspace.

The transformation is defined in such a way that the first principal component has the largest possible variance (that is, accounts for as much of the variability in the data as possible), and each succeeding principle component in turn has the highest variance possible under the constraint that it is orthogonal to the preceding components. The resulting vectors are an uncorrelated orthogonal basis set. PCA is sensitive to the relative scaling of the original variables.

Mathematically, the principal components are the eigenvectors of the covariance or correlation matrix of the original dataset. As the covariance matrix or correlation matrix is symmetric, the eigenvectors are orthogonal. The principal components (eigenvectors) correspond to the direction (in the original n-dimensional space) with the greatest variance in the data.

Each eigenvector has a corresponding eigenvalue. An eigenvalue is a scalar. The corresponding eigenvalue is a number that indicates how much variance there is in the data along that eigenvector (or principal component). A large eigenvalue means that the principal component indicates a large amount of the variance in the data. Similarly, a principal component with a very small eigenvalue indicates a small amount variance in the data.

In some examples, the data are not normalized. In some examples, the data are normalized. If the data are not normalized, attributes with large values and large variances (in absolute terms) will dominate the first principal component. Normalization transforms each attribute into more or less to the same scale, so that each attribute has equal representation during principal component analysis.

Non-limiting examples of how to perform PCA are described in, e.g., Smith, Lindsay I, "A tutorial on principal components analysis." Cornell University, USA 51, 2002, and Shlens, Jonathon, "A tutorial on principal component analysis," arXiv preprint arXiv: 1404.1100 (2014).

To apply principle component analysis in the disclosed methods, a set of data consisting of multiple measurements (e.g., one or more of the light absorption, luminescence, phosphorescence, fluorescence, and chemiluminescence of a urine sample at two or more wavelengths of light) is created for each sample. The set of data for a sample can be represented by a vector. For example, a vector X for Sample i can have measurements of light absorbance at m different wavelengths. Thus, each vector is an m-dimensional vector, where m is the number of element. Each element can be a measurement. The elements in the vector can be the measurements of the same type (e.g., light absorbance at a particular wavelength). They can be measurements of different types, e.g., including both light absorbance and luminescence. In some embodiments, the vector can include elements that represent various characteristics of the sample, e.g., spectroscopic information.

Within this description the index i will be used to denote the wavelength (range 1 to m) and the index j will be used to denote the sample within the data training set ranging from 1 to n. In order to estimate the population variance of spectral data about a specific wavelength, i, of a sample size of n, the statistical moments of each measurement are calculated using, e.g., formula (I) and (II):

$$\mu_i = \sum_{j=1}^{n} X_{ij} P_{ij} \quad \text{(I)}$$

$$\sigma_i^2 = \sum_{j=1}^{n} (X_{ij} - \mu_i)^2 P_{ij} \quad \text{(II)}$$

where $\mu_i$ is the mean, $X_{ij}$ represents the measurement, e.g., spectroscopic information obtained at the denoted wavelength i, for a given sample and $P_{ij}$ is the probability of $X_{ij}$ at that $i^{th}$ wavelength, for that sample. The variance at a specific wavelength, $\sigma_i^2$ is calculated as the $2^{nd}$ central moment about the mean. The $i^{th}$ wavelength refers to a wavelength in a sequential index of wavelengths beginning with the limits of the spectral range. For example, in some embodiments, if i=1, λ=200, the i+1 wavelength can be, e.g., 210 nm or 200.1 nm.

The result of Formula (I) and (II) for each wavelength can form two matrices of dimensions 1×m: the mean and standard deviation arrays denoted U and S, respectively, and contain the population variance information for each type of measurement, e.g., light absorption at different wavelengths as determined by a spectrophotometer.

X is defined as the array of spectral data (e.g. absorbance) at each of m wavelengths for n specimens of the training set (that is, X is a matrix of dimension m×n, with elements $X_{ij}$). Let X' denote the standardized array of spectral data where the values are centered about the corresponding means contained with U and divided by the corresponding standard deviations contained within S. The correlation matrix R is calculated by multiplying the transpose of X' (that is, $X'^T$) with X' and dividing by the degrees of freedom, n−1 (see, e.g., Formula III).

$$R = \frac{X'^T X'}{n-1} \quad \text{(III)}$$

The spectral data matrix X is an i×j matrix with m number of wavelengths and n number of spectral readings. For example, in one embodiment, i=15 and corresponds to the wavelength between 200 nm and 340 nm, at intervals of 10 nm, and j=120, which is the number of samples in an exemplary training set for which there are spectral readings at each wavelength. X' denotes the standardized matrix in which each element is less than the mean and divided by the sample standard deviation.

The matrix W is a spectral data matrix where each element has had subtracted the corresponding element in matrix U. The covariance matrix C was calculated by multiplying the transpose of W (that is $W^T$) with W (see formula IV).

$$C = \frac{W^T W}{n-1} \quad \text{(IV)}$$

C captures the covariance between all possible pairs of measurements (e.g., light absorption at each of m wavelengths). The covariance values reflect the noise and redundancy in the measurements and is contained with a matrix of dimensions m×m.

The eigenvalues[1], $\lambda_i$, for the correlation matrix are calculated and each eigenvector, $B_i$ (with dimension 1×n) for the correlation matrix is determined such that condition V is met:

[1] Note that here $\lambda_i$ refers to the eigenvalue and not to a spectroscopic wavelength. However it is worth noting that for this application these are the eigenvalues corresponding to wavelength ranges in the electromagnetic spectrum.

$$CB_i = \lambda_i B_i \quad \text{(V)}$$

Each eigenvalue represents the amount of variance accounted for in the spectral data sets when normalized by the number of principal components in the data set (equal to the number of measurements). Let B be the matrix for which each column is composed of successive eigenvector ($B_i$) where i ranges from 1 to m. Given that each eigenvector is an m×1 matrix in which each element may also be considered as a regression coefficient for the principal components, B is an m×m matrix containing the information for computation of the principal components of an electromagnetic spectrum composed of n wavelength ranges.

The principal component matrix for each sample Y that can be calculated by matrix multiplication of a matrix B transpose (that is $B^T$) with the standardized spectral data X':

$$Y = B^T X' \quad \text{(VI)}$$

Thus each element of the principal component matrix Y, expressed as $y_{ij}$, is a principal component for a given sample. In this work we have shown that the first four (i=[1, . . . , 4]) principal components contain the majority (>90%) of the variance observed for a sample j.

Clustering Analysis

Some embodiments of any of the methods described herein, further include performing clustering analysis. Clustering is a procedure to group samples in such a way that samples in the same group (called a cluster) are more similar to each other than to those in other groups (clusters). Clustering algorithms include, but are not limited to, hierarchical clustering algorithms, k-means clustering algorithms, and statistical distribution models.

Hierarchical clustering is a method of cluster analysis which seeks to build a hierarchy of clusters. The basic process of hierarchical clustering can include:

(1) Starting by assigning each item to its own cluster, so that for N items, there will be N clusters. Each cluster initially contains just one item. Let the distances (similarities) between the clusters equal the distances (similarities) between the items they contain.
(2) Finding the closest (most similar) pair of clusters and merge them into a single cluster.
(3) Computing distances (similarities) between the new cluster and each of the old clusters.
(4) Repeating steps (2) and (3) until all items are clustered into a single cluster of size N.

Detailed methods of clustering is described in numerous references. See, e.g., D'andrade, "U-Statistic Hierarchical Clustering" Psychometrika 4:58-67, 1978; Johnson, "Hierarchical Clustering Schemes" Psychometrika 2:241-254, 1967; and Borgatti, "How to explain hierarchical clustering," Connections 17 (2): 78-80, 1994.

In some embodiments, k-means clustering can be used to analyze results of principle component analysis. K-means clustering aims to partition n observations into k clusters in which each observation belongs to the cluster with the nearest mean, serving as a prototype of the cluster. This results in a partitioning of the data space into Voronoi cells. In one example, the algorithm proceeds as follows:

(1) Choosing k initial cluster centers (centroid), for example, choosing k observations at random.
(2) Computing point-to-cluster-centroid distances of all observations to each centroid. There are many different ways to compute the distances, e.g., batch update, which assigns each observation to the cluster with the closest centroid; and online update, which individually assigns observations to a different centroid if the reassignment decreases the sum of the within-cluster, sum-of-squares point-to-cluster-centroid distances.
(3) Computing the average of the observations in each cluster to obtain k new centroid locations.
(4) Repeating steps 2 through 3 until cluster assignments do not change, or the maximum number of iterations is reached.

An exemplary detailed method of implementing K-means clustering is described, e.g., in U.S. Pat. No. 6,012,058; Kanungo et al., "An efficient k-means clustering algorithm: Analysis and implementation," IEEE transactions on pattern analysis and machine intelligence 24.7:881-892, 2002.

Furthermore, in some embodiments, clustering can be performed by a standard distribution model, e.g., multivariate normal distributions used by the expectation-maximization (EM) algorithm. The EM iteration alternates between performing an expectation (E) step, which creates a function for the expectation of the log-likelihood evaluated using the current estimate for the parameters, and a maximization (M) step, which computes parameters maximizing the expected log-likelihood found on the E step. These parameter-estimates are then used to determine the distribution of the latent variables in the next E step. Exemplary methods of implementing EM algorithms are described in, e.g., U.S. Pat. No. 6,615,205; WO 2011/162589; Mackay, "Information theory, inference and learning algorithms," Cambridge University Press, 2003.

In some embodiments, the clustering analysis determines whether a urine sample from a subject is grouped or associated with natural urine samples, synthetic urine samples, chemically-adulterated urine samples, lyophilized urine samples, or diluted natural urine samples, and thus determines whether a urine sample from a subject is a natural urine sample, a synthetic urine sample, a chemically-adulterated urine sample, a lyophilized urine sample, or a diluted natural urine sample.

Regression Analysis

Some embodiments of any of the methods described herein, further include performing regression analysis on one or more of the determined light absorption, luminescence, phosphorescence, fluorescence, and chemiluminescence of a urine sample at two or more wavelengths of light, or the data derived therefrom, e.g., results from principle component analysis.

A linear regression equation can be, e.g., expressed as:

$$Y = \alpha + \beta_1 X_1 + \beta_2 X_2 + \ldots + \beta_k X_k + \varepsilon \quad \text{(VII)}$$

Y, the dependent variable, indicates a quantitative measure, e.g., a likelihood score that the sample is a natural urine sample, a synthetic urine sample, a diluted natural urine sample, a lyophilized urine sample, or a chemically-adulterated urine sample. The dependent variable Y depends on k explanatory variables (e.g., one or more of the determined light absorption, luminescence, phosphorescence, fluorescence, and chemiluminescence of a urine sample at two or more wavelengths of light, or results from principle component analysis), plus an error term that encompasses various unspecified omitted factors. In the above-identified model, the parameter $\beta_1$ gauges the effect of the first explanatory variable $X_1$ on the dependent variable Y. $\beta_2$ gives the effect of the explanatory variable $X_2$ on Y.

A logistic regression model is a non-linear transformation of the linear regression. The logistic regression model is often referred to as the "logit" model and can be expressed as:

$$\ln[p/(1-p)] = \alpha + \beta_1 X_1 + \beta_2 X_2 + \ldots + \beta_k X_k + \varepsilon \quad \text{(VIII)}$$

where:

$\alpha$ and $\varepsilon$ are constants, ln is the natural logarithm, $\log_{(e)}$, where $e = 2.71828\ldots$, p is the probability that the event Y occurs, p/(1−p) is the "odds," and ln[p/(1−p)] is the log odds, or "logit."

It will be appreciated by those of skill in the art that $\alpha$ and $\varepsilon$ can be folded into a single constant, and expressed as $\alpha$. In some embodiments, a single term $\alpha$ is used, and $\varepsilon$ is omitted. The "logistic" distribution is an S-shaped distribution function. The logit distribution constrains the estimated probabilities (p) to lie between 0 and 1.

In one embodiment, the logistic regression model is expressed as:

$$Y = \alpha + \sum \beta_i X_i, \quad \text{(IX)}$$

where Y is a value indicating whether a test sample classifies with a group of urine samples, e.g., natural urine samples, synthetic urine samples, lyophilized urine samples, diluted natural urine samples, or chemically-adulterated urine samples, as opposed to another group of urine samples. The probability that a test sample classifies with a particular group of urine samples, as opposed to the other groups, can be derived from Y. The higher the score, the higher the probability that the test sample classifies with the group of interest. Xi is an explanatory variable. In some embodiments, Xi can be results obtained from principle component analysis, e.g., $X_1$ can be the value (coordinate) for the first principle component, $X_2$ can be the value (coordinate) for the second principle component, and $X_3$ can be the value (coordinate) for the third principle component. In some embodiments, Xi can be the one or more of the determined light absorption, luminescence, phosphorescence, fluorescence, and chemiluminescence of a urine sample at two or more wavelengths of light, or data derived therefrom.

In some embodiments, the logistic regression model is fit by maximum likelihood estimation (MLE). The coefficients (e.g., $\alpha$, $\beta 1$, $\beta 2$, . . . ) are determined by maximum likelihood. A likelihood is a conditional probability (e.g., P(Y|X), the probability of Y given X). The likelihood function (L) measures the probability of observing the particular set of dependent variable values (Y1, Y2, . . . , Yn) that occur in the data set. In some embodiments, it is written as the product of the probability of observing Y1, Y2, . . . , Yn:

$$L = Prob(Y1, Y2, \ldots , Yn) = Prob(Y1) * Prob(Y2) * \ldots Prob(Yn) \quad \text{(X)}$$

The higher the likelihood function, the higher the probability of observing the Ys in the sample. MLE involves finding the coefficients ($\alpha$, $\beta 1$, $\beta 2$, . . . ) that make the log of the likelihood function (LL<0) as large as possible or −2 times the log of the likelihood function (−2LL) as small as possible. In MLE, some initial estimates of the parameters $\alpha$, $\beta 1$, $\beta 2$, and so forth are made. Then, the likelihood of the data given these parameter estimates is computed. The parameter estimates are improved, the likelihood of the data is recalculated. This process is repeated until the parameter estimates remain substantially unchanged (for example, a change of less than 0.01 or 0.001). Non-limiting examples of logistic regression and fitting logistic regression models are found in Hastie, "The Elements of Statistical Learning," Springer, N.Y., pp. 95-100, 2001.

Once the logistic regression equation coefficients and the logistic regression equation constant are determined, the model can be readily applied to a test subject to obtain Y. In one embodiment, Y can be used to calculate probability (p) by solving the function Y=ln(p/(1−p)).

Platforms

The present disclosure also provides a platform for determining whether a urine sample comprises or consists essentially of, or is a natural urine sample, a synthetic urine sample, a chemically-adulterated urine sample, a lyophilized urine sample, or a diluted natural urine sample. The platforms can include, e.g., a sample introduction mechanism, a spectrophotometric detection component, and an analysis system.

The sample introduction mechanism is designed for introducing a urine sample (e.g., a urine sample from a subject or a control urine sample of any of the urine sample types described herein) for spectroscopic interrogation and may include manual, automated, physical, or chemical manipulation of the sample. In some embodiments, the introduction of a urine sample includes manual introduction of urine sample (e.g., a urine sample from a subject or a control urine sample of any of the urine sample types described herein) by pipette or syringe, automated introduction of specimen by pipette or syringe using positive displacement, positive pressure, vacuum, suction, siphoning, capillary action, or electrophoresis.

A sample can be introduced into any suitable format for subsequent spectroscopic interrogation including chromatography vials, plastic (e.g., disposable cuvettes), glass cuvettes, quartz cuvettes, 8-well strips, 24-, 48-, 96-, or 384-well or other high-density format plates with optically transparent windows for spectroscopic interrogation, sample containers for automated-analyzer systems, microscope slides, fluidic or microfluidic chambers comprised of polymer materials, glass, quartz, ceramic, stainless steel, or other metal alloys.

Physical manipulation of the samples during sample introduction can include dilution, pre-concentration, evaporation, lyophilization, sonication, ultrasonication, freezing, thawing, or any combination thereof, to prepare the sample for spectroscopic interrogation.

Chemical manipulation of the samples during sample introduction can include flow-injection, liquid-liquid extraction (LLE), supported-liquid extraction (SLE), static headspace extraction, purge and trap, solid-phase extraction (SPE), solid-phase microextraction (SPME), size exclusion chromatography (SEC), protein precipitation, hydrophobic interaction chromatography (HIC), thin layer chromatography (TLC), gas chromatography (GC), fast GC, two-dimensional gas chromatography (GC×GX), super-critical fluid chromatography (SFC), liquid chromatography, high-performance liquid chromatography (HPLC), ultra-high-performance liquid chromatography (UHPLC), two-dimensional liquid chromatography (LC×LC), reverse-phase liquid chromatography (RPLC), normal-phase liquid chromatography, hydrophobic interaction liquid chromatography (HILIC), ion-pairing chromatography, capillary zone electrophoresis (CZE), capillary isoelectric focusing, capillary gel electrophoresis, capillary electrokinetic chromatography, or any combination thereof, prior to spectroscopic interrogation.

In some embodiments, a spectrophotometric detection component includes a stand-alone device or instrument or can be fully-integrated into a device, instrument, system, or platform. A spectrophotometric detection component can include a light source or combination of light sources which emit across any portion or combination of the spectral regions as described herein, a region where spectroscopic interrogation occurs or a region of a device or instrument which performs any of the chemical or physical manipulations of a urine sample, a spectroscopic analyzer which may be a prism, diffraction grating, or set of spectroscopic filters including band-pass, band-stop, or notch filters, or an interferometer, a spectroscopic detector which may be either a phototude, photomuliplier tube, microchannel plate, photographic film, charge-coupled device (CCD), charge-injection device, photoelectric detectors including, e.g., CdZnTe, HgCdTe, photodiode, complementary metal-oxide-semiconductor (CMOS), a photovoltaic device, a thermal detector such as a bolometer, pyroelectric, cryogenic, or Golay detector, the necessary optics including mirrors, lenses, and filters required to reflect, focus, or filter wavelengths of light as they propogate from source through the sample, spectroscopic analyzer, and the detector.

The integrated device instrument or system may be of the following types, a spectrophotometer, a spectroscope, a multi-well spectroscopic plate reader, a fluorimeter, a Fourier-transform infrared spectrometer, a UV-Vis spectrometer, a dispersive near-IR spectrometer, a Vacuum Ultraviolet Spectrometer, a diode-array detector, a CCD Camera, a microscope, a fluorescence microscope, a microfluidic device-coupled spectrometer, a flow-cell detector, a GC detector, an LC-detector, an SFC-detector, an electrophoresis detector, or a hybrid detection platform that combines spectroscopic detection with mass spectrometry.

In some embodiments, the system or platform further includes, e.g., an analysis system that performs a mathematical operation through a coded software process which manipulates the raw spectroscopic information (e.g., one or more of the determined light absorption, luminescence, phosphorescence, fluorescence, and chemiluminescence at two or more wavelengths of light) to give a quantity which is related to the presence of certain biological properties or proportional to the concentration of chemical compounds in natural urine samples, and are differentiable from the quantities yielded by the same algorithm for synthetic urine samples, lyophilized urine samples, diluted natural urine samples, and chemical-adulterated urine samples.

In some embodiments, the methods described herein also includes performing genetic analysis of genetic material present in the urine sample.

In some embodiments, the methods described herein also includes determining a chemical composition of a urine sample by mass spectrometry analysis.

The result obtained by the methods described in this disclosure may be combined mathematically or qualitatively with the results of chemical and physical validity testing including, the level of creatinine, the pH, the concentration of oxidizer(s), the specific gravity, the level of nitrite, the level of glutaraldehyde, the concentration of surfactant(s), or temperature of the urine sample.

Analysis System and Computer Implementation

Any of the methods described herein can be, e.g., a computer-implemented method. In some embodiments, analysis as disclosed in the present disclosure can be implemented in digital electronic circuitry, in tangibly-embodied computer software or firmware, in computer hardware, including the structures disclosed herein and their structural equivalents, or in combinations of one or more thereof. Implementations of the methods described herein can be implemented as one or more computer programs, i.e., one or more modules of computer program instructions encoded on a tangible program carrier for execution by, or to control the operation of, a processing device. Alternatively or in addition, the program instructions can be encoded on a propagated signal that is an artificially generated signal, e.g., a machine-generated electrical, optical, or electromagnetic signal that is generated to encode information for transmission to suitable receiver apparatus for execution by a processing device. A machine-readable medium can be, e.g., a machine-readable storage device, a machine-readable storage substrate, a random or serial access memory device, or a combination of one or more thereof.

In some embodiments of any of the methods described herein, the analysis methods as disclosed herein are implemented in the form of computer program instructions and executed by a processing device. Suitable programming languages for expressing the program instructions include, but are not limited to, C, C++, Java, Python, SQL, Perl, Tcl/Tk, JavaScript, ADA, OCaml, Haskell, Scala, and statistical analysis software, such as SAS, R, MATLAB, SPSS, COARExpress® statistical analysis software, and Stata etc. Various aspects of the methods may be written in different computing languages from one another, and the various aspects are caused to communicate with one another by appropriate system-level-tools available on a given system.

The processes and logic flows described in this specification can be performed by one or more programmable computers executing one or more computer programs to perform functions by operating on input information and generating output. The processes and logic flows can also be performed by, and apparatus can also be implemented as, special purpose logic circuitry, e.g., an FPGA (field programmable gate array), an ASIC (application specific integrated circuit), or RISC.

Computers suitable for the execution of a computer program include, by way of example, general or special purpose microprocessors or both, or any other kind of central processing unit. Generally, a central processing unit will receive instructions and information from a read-only memory or a random-access memory, or both. The essential elements of a computer are a central processing unit for performing or executing instructions and one or more memory devices for storing instructions and information. Generally, a computer will also include, or be operatively coupled to receive information from or transfer information to, or both, one or more mass storage devices for storing information, e.g., magnetic, magneto optical disks, or optical disks.

Computer readable media suitable for storing computer program instructions and information include various forms of non-volatile memory, media, and memory devices, including by way of example semiconductor memory devices, e.g., EPROM, EEPROM, and flash memory devices; magnetic disks, e.g., internal hard disks or removable disks; magneto optical disks; and CD ROM and (Blue Ray) DVD-ROM disks. The processor and the memory can be supplemented by, or incorporated in, special purpose logic circuitry.

To provide for interaction with a user, implementations of the methods described in this specification can be implemented on a computer having a display device, e.g., a CRT (cathode ray tube) or LCD (liquid crystal display) monitor, for displaying information to the user, a keyboard, and a pointing device, e.g., a mouse or a trackball, by which the user can provide input to the computer. Other kinds of devices can be used to provide for interaction with a user as well. In addition, a computer can interact with a user by sending documents to and receiving documents from a device that is used by the user; for example, by sending web pages to a web browser on a user's client device in response to requests received from the web browser.

Implementations of the methods described in this specification can be implemented in a computing system that includes a back end component, e.g., as an information server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital information communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, the server can be in the cloud via cloud computing services.

While this specification includes many specific implementation details, these should not be construed as limitations on the scope of any of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations, one or more features from a combination can in some cases be excised from the combination, and the claimed combination may be directed to a sub-combination or variation of a sub-combination.

Obtaining an Additional Urine Sample

Some embodiments of any of the methods described herein can further include selecting a subject having a urine sample characterized as a synthetic urine sample, a diluted natural urine sample, a chemically-adulterated urine sample, or a lyophilized urine sample, and obtaining an additional urine sample from the selected subject. In some embodiments, the additional urine sample is obtained through a witnessed urine test.

Some embodiments of any of the methods described herein can further include selecting a subject having a urine sample characterized as a synthetic urine sample, a diluted natural urine sample, a chemically-adulterated urine sample, or a lyophilized urine sample, and obtaining a sample including blood, serum, hair, or plasma from the selected subject.

Assays to Determine the Level of One or More Drugs or Drug Metabolites

Some of the methods described herein further include performing an assay to determine the level of one or more (e.g., two, three, four, five, six, or seven) drugs and/or the level one or more (e.g., two, three, four, five, six, or seven) drug metabolites (e.g., any of the exemplary drugs and/or drug metabolites described herein or known in the art) in a sample (e.g., a urine sample identified using any of the methods described herein being a natural urine sample, an additional urine sample (e.g., any of the additional urine samples described herein), or a sample including blood, serum, hair, or plasma).

Non-limiting examples of drugs and drug metabolites include: Δ9-tetrahydrocannabinol, Δ9-tetrahydrocannabino-11-oic acid, 11-hydroxy-Δ9-tetrahydrocannabinol, 11-nor-9-carboxy-Δ9-tetrahydrocannabinol, ethyl glucuronide, ethyl sulfate, morphine-3-glucuronide, morphine-6-glucu-ronide, amitriptyline, morphine 3,6-diglucuronide, morphine 3-ethereal sulfate, normorphine, cyclobenzaprine, norcodeine, codeine, normeperidine, norfentanyl, normorphine 6-glucoronide, 6-monoacetylmorphine, 6-monoacetylmorphine, 3-monoacetylmorphine, buprenorphine, morphine, clobazam, hydromorphone, hydrocodone, norhydrocodone, oxymorphone, normethadol, methadol, EDDP, EMDP, benzoylecgonine, ecgonine methyl ester, norcocaine, carisoprodol, p-hydroxycocaine, m-hydroxycocaine, p-hydroxybenzoylecgonine, m-hydroxybenzoylecgonine, methamphetamine, meperidine, meprobamate, amphetamine, MDMA, MDEA, MDA, 5-(glutathion-S-yl)-alpha-methyldopamine, 2,5-bis(glutathion-S-yl)-alpha-methyldopamine, free HMMA, DHMA sulfate, HMMA glucuronide, 7-aminoflunitrazepam, N-desmethylflunitrazepam, nitrazepam, N-desmethylclomipramine, N-desmethylcyclobenzaprine, doxepin, N-desmethylclobazam, desmethyldoxepin, 3-hydroxyflunitrazepam, gamma-hydroxybutyric acid, D-2-hydroxyglutaric acid, dehydronorketamine, maprotiline, imipramine, norketamine, 4-phenyl-4-(1-piperidinyl)cyclohexanol, dextrorphan, N-acetyl mescaline, ortriptyline, desipramine, 10-OH-nortriptyline, nortriptyline, tramadol, O-desmethyl-cis-tramadol, desmethyl-nortriptyline, fentanyl, phenobarbital, amylobarbitone, 3'-hydroxyamylobarbitone, alpha-hydroxy alprazolam, zopiclone, zolpidem, 7-amino-clonazepam, 4-hydroxymidazolam, loprazolam, flurazepam, flurazepam, 7-aminoflunitrazepam, midazolam, 1-hydroxymidazolam, norbuprenorphine, bromazepam, primidone, alpha-hydroxyalprazolam, 3-hydroxyflunitrazepam, estralozam, pentazocine, alprazolam, lorazepam, clonazepam, triazolam, desalkylfurazepam, flunitrazepam, propoxyphene, protriptyline, ritalinic acid, lormetazepam, alpha-hydroxytriazolam, desmethylflunitrazepam, methadone, diazepam, dothiepin, nordiazepam, oxazepam, methylphenidate, mianserin, naloxone, N-desmethylmirtazapine, mirtazapine, N-desmethyltapentadol, tapentadol, N-desmethyltrimipramine, trimipramine, metagynine, 7-hydroxymitragynine, AM2201, HU-210, JWH-018, JWH-018 5-pentanoic acid metabolite, JWH-073, JWH-073 4-butanoic acid metabolite, JWH-073 N-(3-hydroxybutyl) metabolite, JWH-200, JWH-250, temazepam, marijuana, hashish, heroin, an opiate, cocaine, an amphetamine, phentermine, pregabalin, methamphetamine, a MDMA, flunitrazepam, GHB, ketamine, PCP, Salvia divinorum, dextromethorphan, dextromorphan, LSD, mescaline, psilocybin, mephedrone, methylone, 3,4,-methylenedioxypyrovalerone (MDPV), an anabolic steroid, an inhalant, acetaminophen, hydrocodone, noroxycodone, oxycodone, tricyclic antidepressants, barbituates, and benzodiazepines.

A variety of urine drug assays and urine drug metabolite assays are commercially available. For example, urine drug metabolite assays can be purchased from American Screening Corp., Ameritox, Confirm Biosciences, Alibaba, Rapid Exams, and DrugConfirm.

An assay to determine the level of one or more drugs and/or the level of one or more drug metabolites in a urine sample (e.g., any of the urine samples described herein from any subject described herein) can be performed at the same time as a method to characterize the urine sample as a natural urine sample, a synthetic urine sample, a diluted natural urine sample, a chemically-adulterated urine sample, or a lyophilized urine sample (e.g., using any of the methods of characterizing a urine sample provided herein).

As is well known in the art, the determined level of the one or more drugs and/or the determined level of the one or more drug metabolites can be compared to reference values of the one or more drugs and/or the one or more drug metabolites (e.g., the level of the one or more drugs and/or the level of one or more drug metabolites in a subject that has not been administered a drug and/or an agent that is not metabolized into the one or more drug metabolites).

Some of the methods described herein also include methods of performing a principle component analysis on a natural urine sample containing a drug and/or a drug metabolite. As certain drugs or drug metabolites have characteristic spectra, the methods described in the present disclosure, e.g., principle component analysis, can also be used to distinguish natural urine samples urine including or not including drugs and drug metabolites.

Some embodiments of the methods where a subject is identified as having an elevated level of one or more drug metabolites in the natural urine sample, the additional urine sample, or the sample including blood, serum, hair, or plasma, can further include admitting the subject into a drug dependency program, ceasing administration of the controlled substance to the subject, or reducing the dose or frequency of administration of the controlled substance to the subject. In some embodiments, the drug dependency program includes administering to the subject a drug replacement therapy.

Additional Exemplary Steps

Some embodiments of any of the methods described herein can further include recording the characterization of the urine sample in a subject's medical record (e.g., a computer readable medium). Some embodiments of any of the methods described herein further include notifying the subject's insurance provider, employer, or potential future employer of the characterization of the urine sample. Some embodiments of any of the methods described herein further including notifying a pharmacist or a medical professional of the characterization of the urine sample.

Some embodiments of any of the methods described herein can include amplifying and sequencing nucleic acid present in the urine sample. For example, some embodiments of the methods further include: (a) providing a urine sample from a subject; (b) enriching the urine sample for mammalian cells, if present; (c) isolating any genomic DNA from the enriched sample of step (b) to form an isolated genomic DNA test sample; (d) adding to the isolated genomic DNA test sample of step (c) a control DNA to form a control sample or adding the control DNA to the enriched sample of step (b) and then isolating DNA to form a control sample; (e) performing an assay to determine the presence of genomic DNA in the isolated genomic DNA sample of step (c) or the control sample of step (d); (f) performing an assay to determine the presence of the control DNA in the control sample of step (d); and (g) identifying a urine sample having no detectable level of genomic DNA and having detectable control DNA as including, consisting essentially or, or consisting of synthetic urine, or identifying a urine sample having a detectable level of genomic DNA and having detectable control DNA as not including a synthetic urine. Non-limiting examples of the above steps are described in U.S. Patent Application Publication No. 2016/0145684, incorporated herein by reference in its entirety.

Some embodiments of the methods provided herein further include matching a urine sample to a subject that include: (a) providing a urine sample from a subject; (b) enriching the urine sample for mammalian cells, if present; (c) isolating any genomic DNA from the enriched sample of step (b) to form an isolated genomic DNA test sample; (d) adding to the isolated genomic DNA test sample of step (c) a control DNA to form a control sample or adding the control DNA to the enriched sample of step (b) and then isolating the DNA to form a control sample; (e) performing an assay to determine the genotype of at least 6 single nucleotide polymorphisms (SNPs) in the isolated genomic DNA test sample of step (c) or the control sample of step (d); (f) comparing the genotype of the at least 6 SNPs in the isolated genomic DNA test sample of step (c) or the control sample of step (d) with the genotype of the at least 6 SNPs in a control cell sample (e.g., a buccal cell sample) from the subject; (g) performing an assay to determine the presence of the control DNA in the control sample of step (d); and (h) identifying a urine sample having a detectable level of the control DNA and having the same genotype of the at least 6 SNPs in the isolated genomic DNA test sample of step (c) or the control sample of step (d) as the genotype of the at least 6 SNPs in the control cell sample as originating from the subject; or identifying a urine sample having a detectable level of the control DNA and not having the same genotype of the at least 6 SNPs in the isolated genomic DNA test sample of step (c) or the control sample of step (d) as the genotype of the at least 6 SNPs in the control cell sample as not originating from the subject. Non-limiting examples of the above steps are described in U.S. Patent Application Publication No. 2016/0145684, incorporated herein by reference in its entirety.

Some embodiments of any of the methods described herein can further include detecting one or more of statherin, alpha-amylase, and lysozyme in a urine sample. Statherin is a unique phoshoprotein found in saliva. Human statherin is 62 amino acids in length. The human statherin protein sequence is shown below. A variety of antibodies that specifically bind to human statherin are commercially available (e.g., antibodies available from Santa Cruz Biotech, Abcam, and Acris).

```
Human Statherin Protein
                                       (SEQ ID NO: 1)
mkflvfafil almvsmigad sseekflrri grfgyqvgpy qpvpeqplyp qpyqpqyqqy tf
```

Human alpha-amylase is another protein that is present in saliva. Human alpha-amylase is 511 amino acids. The human alpha-amylase protein sequence is shown below. A variety of antibodies that specifically bind to human alpha-amylase are commercially available (e.g., antibodies available from BioVision, AbCam, Sigma-Aldrich, Novus Biologicals, and New England Biolabs).

```
Human Alpha-Amylase Protein
                                       (SEQ ID NO: 2)
mkfflllfti gfcwaqvspn tqqqrtsivh lfewrwvdia lecerylapk gfggvqvspp nenvaiynpf rpwweryqpv syklctrsgn edefrnmvtr cnnvgvriyv davinhmcgn avsagtsstc gsyfnpgsrd fpavpysgwd fndgkcktgs gdienyndat gyrdcrltgl ldlalekdyv rskiaeymnh lidigvagfr ldaskhmwpg dikaildklh nlnsnwfpag skpfiyqevi dlggepikss dyfgngrvte fkygaklgtv irkwngekms ylknwgegwg fvpsdralvf vdnhdnqrgh gaggasiltf wdarlykmav qfmlahpyqf trvmssyrwp rgfqngndvn dwygppnnng vikevtinpd ttcgndwvce hrwrqirnmv ifrnvvdgqp ftnwydngsn qvafgrgnrg fivfnnddws fsltlqtglp agtycdvisg dkingnctgi kiyvsddgka hfsisnsaed pfiaihaesk l
```

Human lysozyme is another protein that is present in saliva. Human lysozyme is 148 amino acids. The human lysozyme protein sequence is shown below. A variety of antibodies that specifically bind to human lysozyme are commercially available (e.g., antibodies available from AbCam, Thermo Scientific, Novus Biologicals, and AbD Serotec).

```
Human Lysozyme
                                       (SEQ ID NO: 3)
mkalivlglv llsvtvqgkv fercelartl krlgmdgyrg islanwmcla kwesgyntra tnynagdrst dygifqinsr ywcndgktpg avnachlscs allqdniada vacakrvvrd pqgirawvaw rnrcqnrdvr qyvqgcgv
```

As is well-known in the art, a variety of antibody-based assays can be used to determine the presence of one or more of statherin, alpha-amylase, and lysozyme) in a urine sample. Non-limiting examples of antibody-based assays include enzyme-linked immunosorbent assays, immunoblotting, protein chip, beads (e.g., magnetic beads) that are coated with an antibody, immunoelectrophoresis, and immunoprecipitation. For example, any of the exemplary antibodies that bind specifically to one of statherin, alpha-amylase, or lysozyme can be used in any of the antibody-based assays described herein or known in the art to determine the presence or level of statherin, alpha-amylase, or lysozyme in a urine sample.

Additional assays for determining the presence or level of one or more statherin, alpha-amylase, and lysozyme in a urine sample are well known in the art and include without limitation: mass spectrometry, enzyme activity assays (e.g., using a detectable substrate or product), electrophoresis, and protein sequencing.

EXAMPLES

The invention is further described in the following examples, which do not limit the scope of the invention described in the claims.

Example 1. Methods of Characterizing a Urine Sample from a Subject

Experiments were performed to determine whether ultraviolet light absorbance of a urine sample can be used to determine if a urine sample is a natural urine sample, a lyophilized urine sample, a diluted natural urine sample, a synthetic urine sample, or a chemically-adulterated urine sample.

The light absorption spectra of natural urine samples, lyophilized urine samples, diluted natural urine samples, synthetic urine samples, and chemically-adulterated urine samples were obtained by spectrophotometers. FIG. 1 shows absorbance spectra of natural urine sample from humans. The absorbance characteristics can be described qualitatively as strong absorbance throughout the ultraviolet region, particularly at wavelengths centered on 240, 280 and 300 nm. Without wishing to be bound by theory, it has been hypothesized that the strong ultraviolet absorption characteristics are due to the presence of one or more of: 1-aliphatic acyclic compounds, aliphatic heteromonocyclic compounds, aliphatic heteropolycyclic compounds, aliphatic homomonocyclic compounds, aliphatic homopolycyclic compounds, alkaloids and derivatives, amino acids, peptides and analogues, aromatic heteromonocyclic compounds, aromatic heteropolycyclic compounds, aromatic homomonocyclic compounds, aromatic homopolycyclic compounds, carbohydrates and carbohydrate conjugates, homogenous metal compounds, homogenous non-metal compounds, inorganic compounds, lignans and norlignans, lipids, mixed metal/non-metal compounds, nucleosides, nucleotides and analogs, organic acids and derivatives, organic halides, organometallic compounds, organophosphorous compounds, polyketides, tannins, bile acids, degradation or chemical-reaction, or enzymatic-reaction products of any of the above, or other compounds both endogenous and xenobiotic in urine occurring due to metabolic processes.

While absorbance is directly proportional to concentration, the majority of urine samples show a saturation effect due to the relatively high concentration of chemical species that strongly absorb ultraviolet light.

Figure 4:
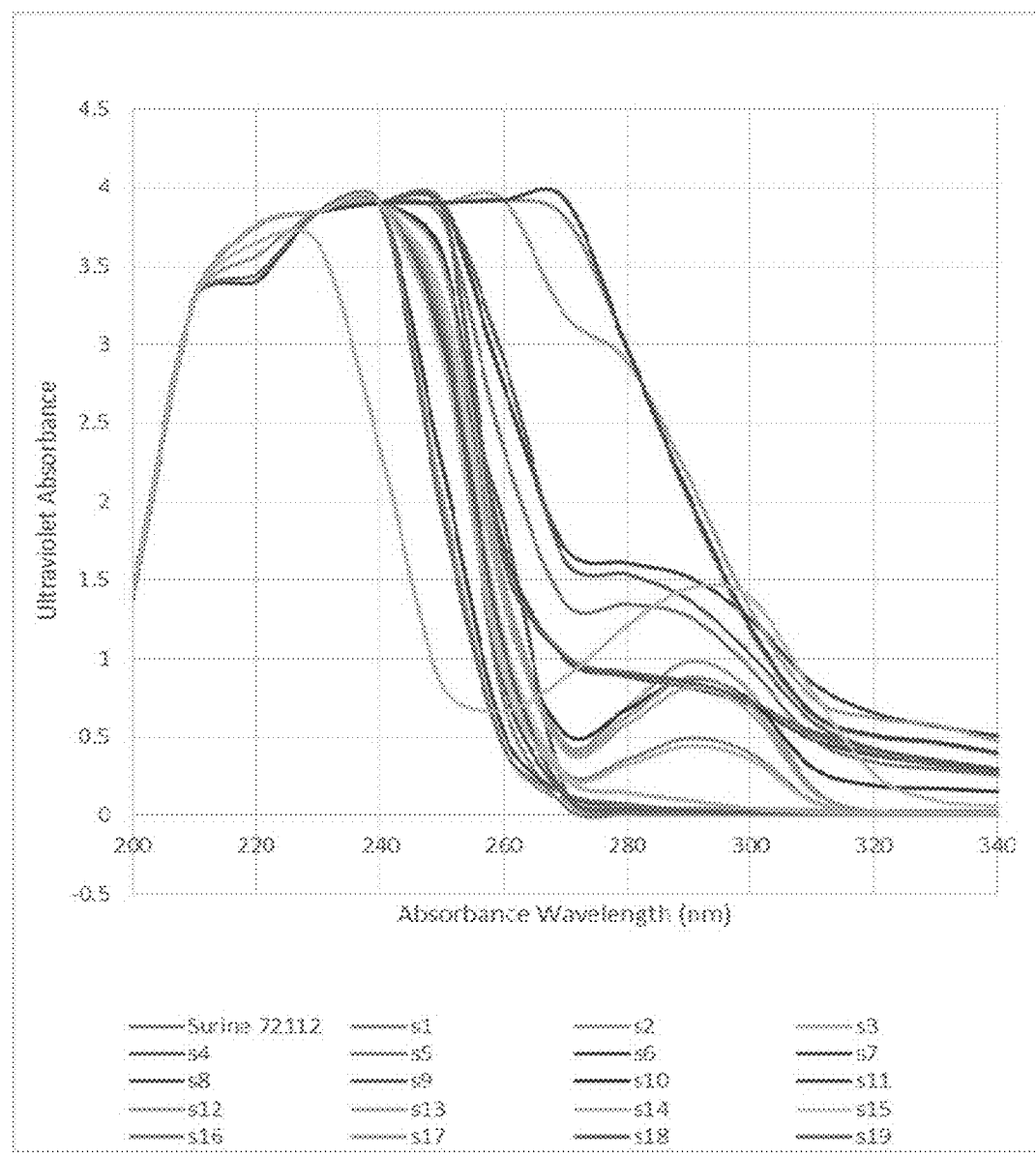
FIG. 4 is a graph showing characteristic ultraviolet absorbance spectra for lyophilized urine samples, diluted natural urine samples, synthetic urine samples, or chemically-adulterated urine samples.

FIG. 4 shows ultraviolet absorption spectra for lyophilized urine samples, diluted natural urine samples, synthetic urine samples, and chemically-adulterated urine samples.

A dataset, containing the light absorption spectrum of these urine samples, was created in order to establish and estimate of the population variance. Each item in the training data set is a spectrum which contains absorbance at multiple wavelengths. In order to estimate the population variance of a sample size of n, the statistical moments of each wavelength were calculated using formula (I) and (II):

$$\mu_i = \sum_{j=1}^{n} X_{ij} P_{ij} \quad \text{(I)}$$

$$\sigma_i^2 = \sum_{j=1}^{n} (X_{ij} - \mu_i)^2 P_{ij} \quad \text{(II)}$$

wherein $\mu_i$ is the mean, $X_{ij}$ represents the measurement, e.g., spectroscopic information obtained at the denoted wavelength i, for a given sample and $P_{ij}$ is the probability of $X_{ij}$ at that $i^{th}$ wavelength, for that sample. The variance at a specific wavelength, $\sigma_i^2$ is calculated as the $2^{nd}$ central moment about the mean.

The result of Formula (I) and (II) for each wavelength formed two arrays: the mean and standard deviation arrays denoted U and S for absorbance at each wavelength.

X is defined as the array of spectral data (e.g. absorbance) at each of m wavelengths for n specimens of the training set (that is, X is a matrix of dimension m×n, with elements $X_{ij}$). Let X' denote the standardized array of spectral data where the values are centered about the corresponding means contained with U and divided by the corresponding standard deviations contained within S. The correlation matrix R is calculated by multiplying the transpose of X' (that is, $X'^T$) with X' and dividing by the degrees of freedom, n−1 (see, e.g., Formula III).

$$R = \frac{X'^T X'}{n-1} \quad \text{(III)}$$

The spectral data matrix X is a i×j matrix with m number of wavelengths and n number of spectral readings. For example, in one embodiment, where i=15 and corresponds to the wavelength between 200 nm and 340 nm at intervals of 10 nm, and j=120, which is an exemplary number of samples in the training set for which there are spectral readings at each wavelength. X' denotes the standardized matrix, in which each element is less than the mean and is divided by the sample standard deviation.

The matrix W is a spectral data matrix where each element has had subtracted the corresponding element in matrix U. The covariance matrix C was calculated by multiplying the transpose of W (that is $W^T$) with W (see formula IV).

$$C = \frac{W^T W}{n-1} \quad \text{(IV)}$$

C captures the covariance between all possible pairs of measurements (e.g., light absorption at each of n wavelengths). The covariance values reflect the noise and redundancy in the measurements and is contained with a matrix of dimensions m×m.

The eigenvalues[2], $\lambda_i$, for the correlation matrix are calculated and each eigenvector, $B_i$ (with dimension 1×m) for the correlation matrix is determined such that condition V is met:

[2] Note that here $\lambda_i$ refers to the eigenvalue and not to a spectroscopic wavelength. However it is worth noting that for this application these are the eigenvalues corresponding to wavelength ranges in the electromagnetic spectrum.

$$CB_i = \lambda_i B_i \quad \text{(V)}$$

Figure 3:
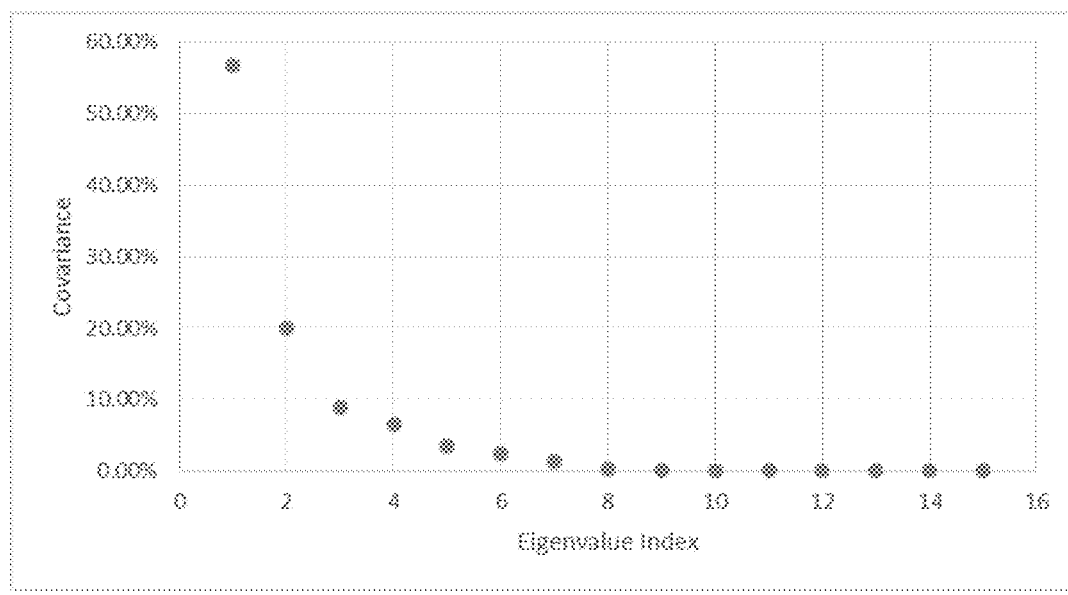
FIG. 3 is a Scree Plot indicating the % of total variance observed in natural urine samples, lyophilized urine samples, diluted natural urine samples, synthetic urine samples, and chemically-adulterated urine samples per principal component (or eigenvalue). These results indicate that 86% of the variance in the characteristic spectra of natural urine samples, lyophilized urine samples, diluted natural urine samples, synthetic urine samples, and chemically-adulterated urine samples can be accounted for by the first three principle components.

FIG. 3 is a Scree Plot indicating the % of total variance observed in a typical sample set per principal component (or eigenvalue). These results indicate that 86% of the variance in the characteristic spectra of natural urine samples, lyophilized urine samples, diluted natural urine samples, synthetic urine samples, and chemically-adulterated urine samples can be accounted for by the first three principle components.

Table 1 shows the extent to which each wavelength range contributes to a specific principal component. For the tested urine samples, principal component 1 correlates with the variance observed between 260 and 300 nm, where as principal component 2 is composed chiefly of the variance at 230-250 nm. Thus, the first two principal components correlate or anti-correlate with wavelengths centered at 280-300 nm and 240 nm. This explains why simpler algorithms based upon the ratio or relative absorbance at 240 nm and 280 nm can be useful.

TABLE 1

The eigenvalues for the first 4 principal components are shown (2nd row, grey box). The eigenvectors for the correlation matrix show which of the principal components give rise to the most variance in each spectral region. Eigenvectors with absolute value >0.3 have been highlighted to indicate the relationships.

| $\lambda$ (nm) | $\epsilon_1$ 8.526359185 | $\epsilon_2$ 3.010215805 | $\epsilon_3$ 1.324644831 | $\epsilon_4$ 0.994120112 |
|---|---|---|---|---|
| 200 | 0.034623586 | −0.159491402 | 0.321332164 | 0.858766315 |
| 210 | 0.11690475 | 0.170090436 | 0.608180694 | −0.108715591 |
| 220 | −0.123168703 | 0.227883361 | 0.604015091 | −0.248533682 |
| 230 | 0.013949483 | 0.551478495 | −0.19076237 | 0.1572497 |
| 240 | 0.012596323 | 0.551082751 | −0.191034495 | 0.160662149 |
| 250 | −0.20050724 | 0.435270894 | 0.140259216 | −0.045323324 |
| 260 | −0.314971054 | 0.124505969 | 0.06743741 | 0.235687282 |
| 270 | −0.318209273 | 0.00130829 | −0.056344378 | 0.183002047 |
| 280 | −0.328638531 | −0.044062678 | −0.010629273 | 0.116787428 |
| 290 | −0.324398063 | −0.101867851 | 0.084267126 | 0.023132726 |
| 300 | −0.305410201 | −0.174520286 | 0.140254063 | −0.080321726 |
| 310 | −0.315927261 | −0.175945449 | 0.027782547 | −0.129656334 |
| 320 | −0.328297643 | −0.021809147 | −0.088052023 | −0.083989453 |
| 330 | −0.328674789 | 0.049497719 | −0.11421298 | −0.042247557 |
| 340 | −0.326824678 | 0.065250359 | −0.115296519 | −0.032003884 |

The principal component matrix for each sample Y that can be calculated by matrix multiplication of a matrix B transpose (that is $B^T$) with the standardized spectral data X':

$$Y = B^T X' \quad\quad\quad (VI)$$

Thus each element of the principal component matrix Y, expressed as $y_{ij}$, is a principal component for a given sample. In this work we have shown that the first four (i=[1, ..., 4]) principal components contain the majority (>90%) of the variance observed for a sample j.

Figure 2:
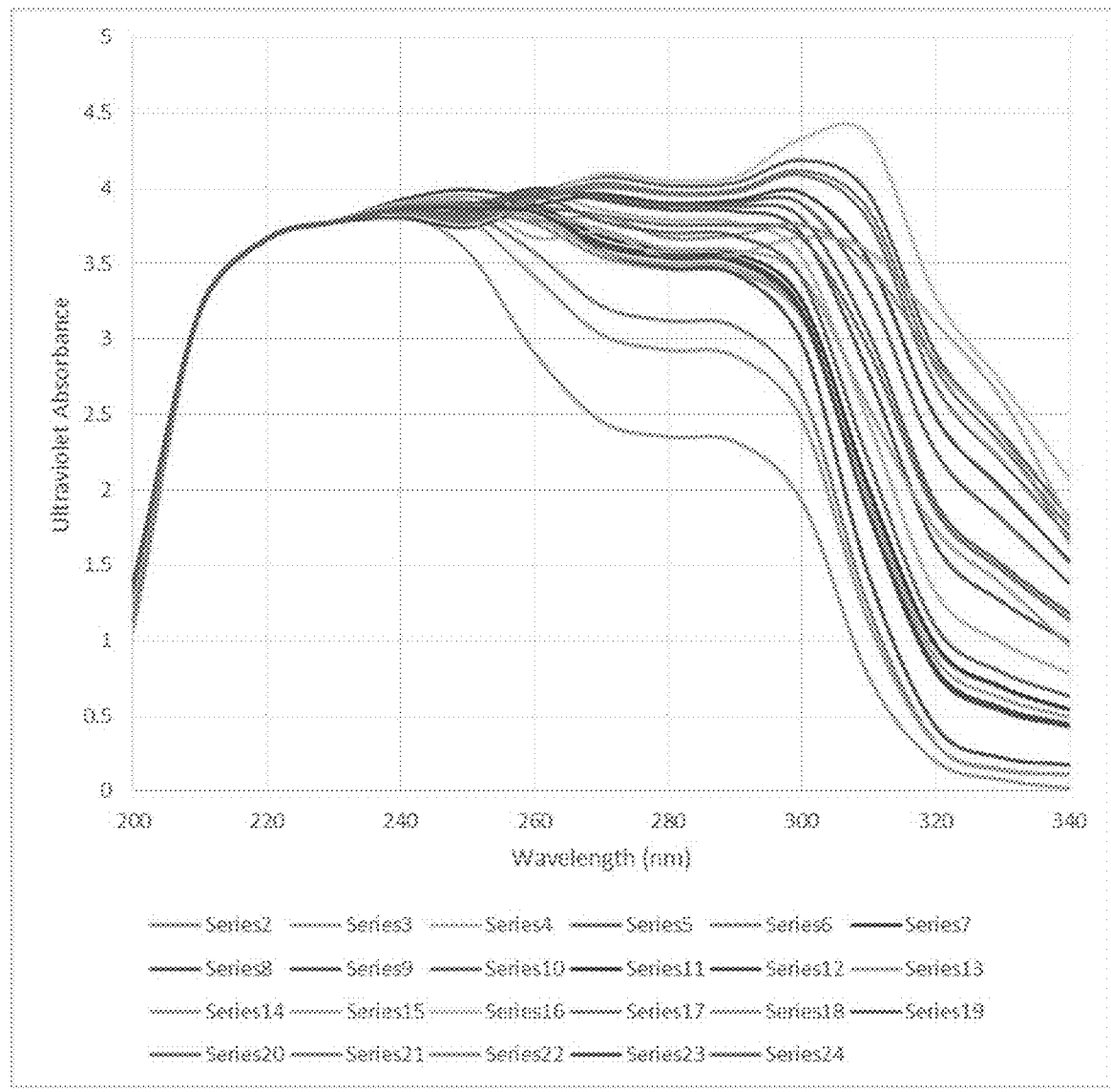
FIG. 2 is a graph showing model spectra of natural urine samples generated by the results from principal component analysis. Principal component analysis reveals that the four primary principal components can be used to construct the model spectra. These model spectra are in good agreement with the raw data shown in FIG. 1, although there is a sizable reduction in the noise that does not contribute to distinguishable variance between the samples.
Figure 5:
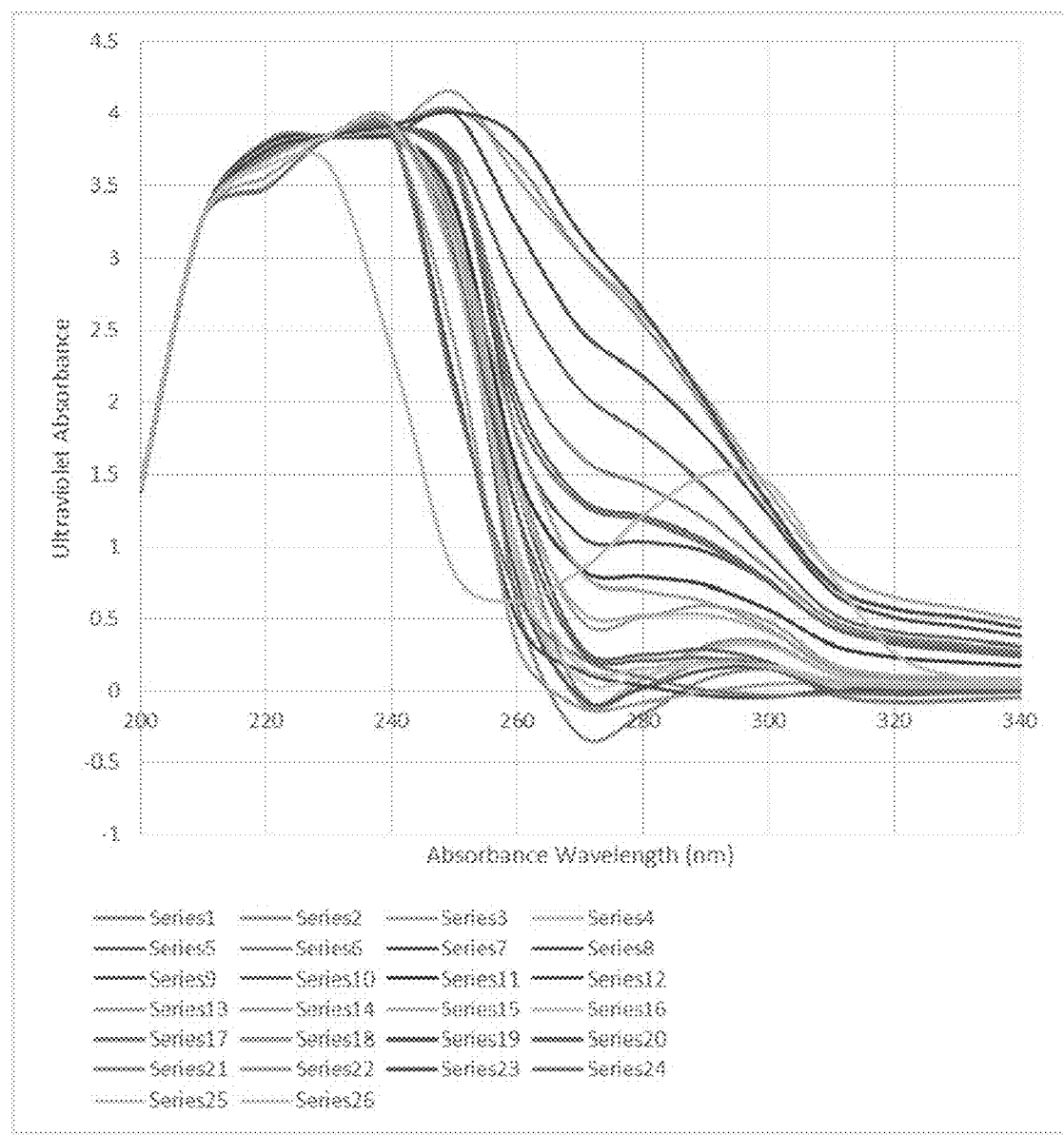
FIG. 5 is a graph showing model spectra generated from the results of principle component analysis. The model spectra is based upon a reduced data set of only 4 of 15 principle components. These principle components account for enough variation of absorbance spectra of the lyophilized urine samples, diluted natural urine samples, synthetic urine samples, and chemically-adulterated urine samples as shown in FIG. 4 and the model spectra accurately reproduces major spectroscopic features in the wavelength range of 200 to 340 nm.

Using the first 4 principal components, a reduced data model of the spectral information was reconstructed for each urine sample. FIGS. 2 and 5 show how well the original raw data (the raw data from FIGS. 1 and 4, respectively) can be represented by a subset of principal components. As expected, the reduced data model captures the key spectral features of the original data (compare FIGS. 2 and 5 to FIGS. 1 and 4, respectively).

Figure 6:
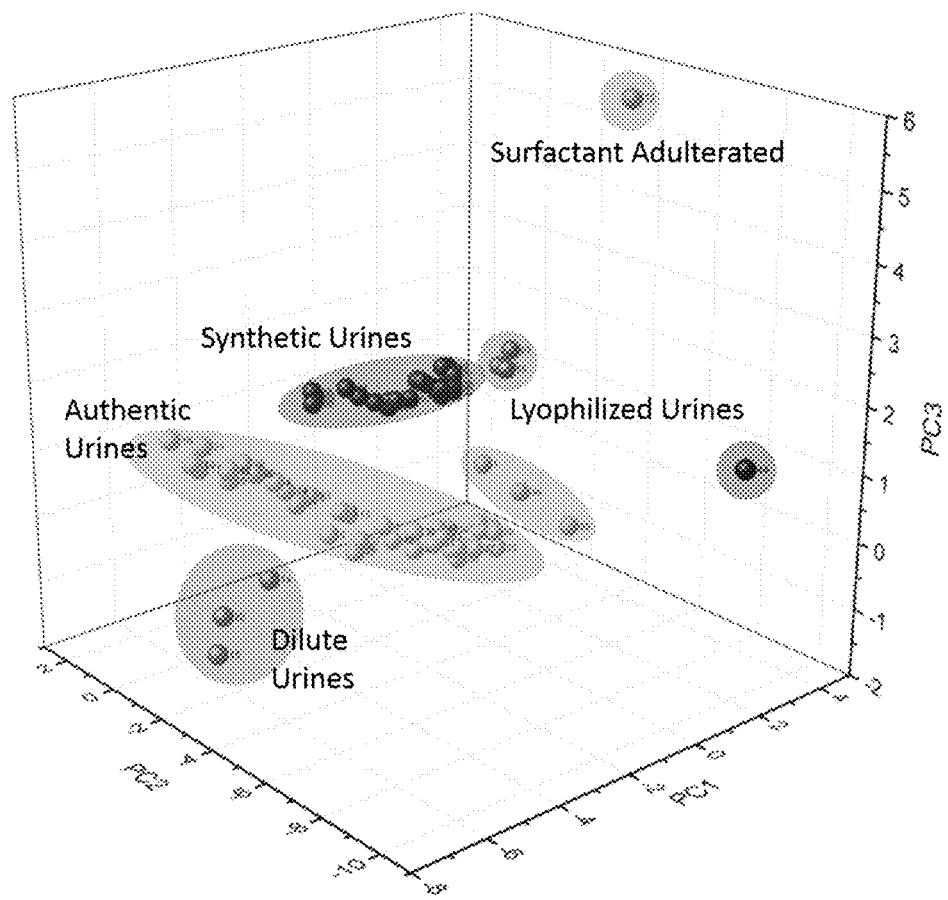
FIG. 6 is a graph showing a cluster plot for natural urine samples, lyophilized urine samples, diluted natural urine samples, synthetic urine samples, and chemically-adulterated urine samples based on the three principle components associated with the variation in spectroscopic data.

A principal component cluster plot was constructed using the first three principal components. FIG. 6 shows a cluster plot for lyophilized urine samples, diluted natural urine samples, synthetic urine samples, and chemically-adulterated urine samples based on the three principle components. Statistical analysis of these clusters were used to differentiate urine samples into different categories.

Example 2. Characterizing Synthetic and Chemically-Adulterated Urine Samples from a Subject As shown in Example 1, principal components 1 and 2 account for 75% of the sample variance, and the first principal component correlates with the variance observed between 260 nm and 300 nm, and the second principal component correlates with the variance observed between 230 nm and 250 nm. Thus, new algorithms were developed to differentiate synthetic urine from a natural urine sample by determining the relationship between absorbance at a wavelength between 260 and 300 nm and the absorbance at a wavelength between 230 and 250 nm.

Absorbance at 240 nm and 280 nm are determined, and Formulas (XIII) and (XIV) are applied to these data.

$$SynScore\ 1 = \frac{\lambda_{240}}{\lambda_{280}} \quad\quad\quad (XIII)$$

$$SynScore\ 2 = 10 \times \log\left(\frac{\lambda_{240}}{\lambda_{280}}\right) \quad\quad\quad (XIV)$$

If SynScore 1 is greater than 3, it indicates that the sample may be a synthetic urine sample due to low UV absorbance at 280 nm.

SynScore 2 is based on the logarithm of the absorbance ratio. SynScore 2 ranges from approximately 0 to about 50. For SynScore 2, a value greater than 5 indicates that sample is a synthetic urine sample. SynScore 2 for a natural urine sample ranges from 0 to 1.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of testing a urine sample from a subject, the method comprising:
  (a) providing a urine sample from a subject;
  (b) determining one or more of the light absorption, luminescence, phosphorescence, fluorescence, and chemiluminescence of the urine sample at two or more wavelengths of light;
  (c) applying one or more eigenvectors derived from a principle component algorithm to a standardized dataset derived from the determined light absorption, luminescence, phosphorescence, fluorescence, and chemiluminescence of the urine sample to generate a Urine Characterization Index (UCI) comprising one or more values for corresponding principle component(s);
  (d) characterizing a urine sample as a natural urine sample based on the UCI; and
  (e) performing testing on the urine sample.

2. The method of claim 1, wherein step (b) comprises determining the light absorption of the urine sample.

3. The method of claim 2, wherein step (b) comprises determining the light absorption of one or more of ultraviolet light wavelength(s), visible light wavelength(s), near-infrared light wavelength(s), and infrared absorption light wavelengths.

4. The method of claim 2, wherein step (b) comprises determining the light absorption of the urine sample at wavelengths of about 200 nm to about 1000 nm.

5. The method of claim 2, wherein step (b) comprises determining the light absorption of the urine sample at wavelengths of about 200 nm to about 340 nm.

6. The method of claim 2, wherein step (c) comprises applying an eigenvector derived from the principle component algorithm to a dataset derived from the determined light absorption to generate a value for one principle component.

7. The method of claim 1, wherein step (c) comprises applying two eigenvectors derived from the principle component algorithm to a dataset derived from the determined light absorption, luminescence, phosphorescence, fluorescence, chemiluminescence, or bioluminescence to generate values in two-dimensional principle component space.

8. The method of claim 7, wherein step (c) comprises applying two eigenvectors derived from the principle component algorithm to a dataset derived from the determined light absorption to generate values in two-dimensional principle component space.

9. The method of claim 1, wherein step (c) comprising applying three eigenvectors derived from the principle component algorithm to a dataset derived from the determined light absorption, luminescence, phosphorescence, fluorescence, chemiluminescence, or bioluminescence to generate values in three-dimensional principle component space.

10. The method of claim 9, wherein step (c) comprises applying three eigenvectors derived from the principle component algorithm to a dataset derived from the determined light absorption to generate values in three-dimensional principle component space.

11. The method of claim 1, wherein step (c) comprising applying four eigenvectors derived from the principle component algorithm to a dataset derived from the determined light absorption, luminescence, phosphorescence, fluorescence, chemiluminescence, or bioluminescence to generate values in four-dimensional principle component space.

12. The method of claim 11, wherein step (c) comprises applying four eigenvectors derived from the principle component algorithm to a dataset derived from the determined light absorption to generate values in four-dimensional principle component space.

13. The method of claim 1, wherein step (d) comprises characterizing a urine sample through the use of a clustering algorithm.

14. The method of claim 13, wherein the clustering algorithm is a hierarchical clustering algorithm, a k-means clustering algorithm, or a statistical distribution model.

15. The method of claim 1, wherein step (d) comprises characterizing a urine sample by performing regression analysis on the values of principle components.

16. The method of claim 1, wherein step (d) comprises comparing the UCI of the sample to a UCI of a natural urine sample.

17. A method of testing a urine sample from a subject, the method comprising:
  (a) providing a urine sample collected from a subject;
  (b) determining the absorbance at a first wavelength (A1) and the absorbance at a second wavelength (A2) of the urine sample, wherein the first wavelength is from about 230 nm to 250 nm, and the second wavelength is from about 260 nm to 340 nm;
  (c) applying an algorithm to the determined A1 and the determined A2 to generate a Urine Characterization Score (UCS), wherein the algorithm includes a ratio of the determined A1 to the determined A2;
  (d) characterizing a urine sample as a natural urine sample based on the UCS; and
  (e) performing testing on the urine sample.

18. The method of claim 17, wherein the UCS is generated using the Formula $$UCS = A1/A2. \qquad \text{(XI)}$$

19. The method of claim 17, wherein the UCS is generated using the Formula $$UCS = 10 \times \log(A1/A2). \qquad \text{(XII)}$$

20. The method of claim 17, wherein the first wavelength is 240 nm and the second wavelength is 280 nm.

21. The method of claim 18, wherein step (d) comprises charactering the urine sample as a synthetic urine sample if UCS is greater than 0.8.

22. The method of claim 19, wherein step (d) comprises charactering the urine sample as a synthetic urine sample if the UCS is less than 0.25.

23. The method of claim 1, wherein the testing in step (e) comprises drug testing.

24. The method of claim 1, wherein the testing in step (e) comprises chemical and physical testing.

25. The method of claim 17, wherein the testing in step (e) comprises drug testing.

26. The method of claim 17, wherein the test in step (e) comprises chemical and physical testing.

* * * * *

SEQUENCE LISTING

```
Sequence total quantity: 3
SEQ ID NO: 1            moltype = AA  length = 62
FEATURE                 Location/Qualifiers
source                  1..62
                        mol_type = protein
                        organism = Homo sapiens
SEQUENCE: 1
MKFLVFAFIL ALMVSMIGAD SSEEKFLRRI GRFGYGYGPY QPVPEQPLYP QPYQPQYQQY  60
TF                                                                62

SEQ ID NO: 2            moltype = AA  length = 511
FEATURE                 Location/Qualifiers
source                  1..511
                        mol_type = protein
                        organism = Homo sapiens
SEQUENCE: 2
MKFFLLLFTI GFCWAQYSPN TQQGRTSIVH LFEWRWVDIA LECERYLAPK GFGGVQVSPP  60
NENVAIYNPF RPWWERYQPV SYKLCTRSGN EDEFRNMVTR CNNVGVRIYV DAVINHMCGN  120
AVSAGTSSTC GSYFNPGSRD FPAVPYSGWD FNDGKCKTGS GDIENYNDAT QVRDCRLTGL  180
LDLALEKDYV RSKIAEYMNH LIDIGVAGFR LDASKHMWPG DIKAILDKLH NLNSNWFPAG  240
SKPFIYQEVI DLGGEPIKSS DYFGNGRVTE FKYGAKLGTV IRKWNGEKMS YLKNWGEGWG  300
FVPSDRALVF VDNHDNQRGH GAGGASILTF WDARLYKMAV GFMLAHPYGF TRVMSSYRWP  360
RQFQNGNDVN DWVGPPNNNG VIKEVTINPD TTCGNDWVCE HRWRQIRNMV IFRNVVDGQP  420
FTNWYDNGSN QVAFGRGNRG FIVFNNDDWS FSLTLQTGLP AGTYCDVISG DKINGNCTGI  480
KIYVSDDGKA HFSISNSAED PFIAIHAESK L                                511

SEQ ID NO: 3            moltype = AA  length = 148
FEATURE                 Location/Qualifiers
source                  1..148
                        mol_type = protein
                        organism = Homo sapiens
```

-continued

```
SEQUENCE: 3
MKALIVLGLV  LLSVTVQGKV  FERCELARTL  KRLGMDGYRG  ISLANWMCLA  KWESGYNTRA   60
TNYNAGDRST  DYGIFQINSR  YWCNDGKTPG  AVNACHLSCS  ALLQDNIADA  VACAKRVVRD  120
PQGIRAWVAW  RNRCQNRDVR  QYVQGCGV                                        148
```